(12) United States Patent
Weickert et al.

(10) Patent No.: US 7,049,406 B2
(45) Date of Patent: May 23, 2006

(54) HEMOGLOBIN MUTANTS WITH INCREASED SOLUBLE EXPRESSION AND/OR REDUCED NITRIC OXIDE SCAVENGING

(75) Inventors: Michael J Weickert, Belmont, CA (US); Christopher B Glascock, Louisville, CO (US); Antony J Mathews, Houston, TX (US); Douglas D Lemon, Louisville, CO (US); Daniel H Doherty, Boulder, CO (US); John S Olson, Houston, TX (US)

(73) Assignees: Baxter Biotech Technology SARL, Neuchatel (CH); William Marsh Rice University, Houston, TX (US)

( * ) Notice: Subject to any disclaimer, the term of this patent is extended or adjusted under 35 U.S.C. 154(b) by 377 days.

(21) Appl. No.: 10/107,871

(22) Filed: Mar. 27, 2002

(65) Prior Publication Data
US 2003/0017537 A1    Jan. 23, 2003

Related U.S. Application Data

(62) Division of application No. 09/403,208, filed as application No. PCT/US98/08861 on May 1, 1998, now Pat. No. 6,455,676.

(60) Provisional application No. 60/057,986, filed on Sep. 5, 1997, provisional application No. 60/045,364, filed on May 2, 1997.

(51) Int. Cl.
*C07K 14/00* (2006.01)
(52) U.S. Cl. ................................ 530/385
(58) Field of Classification Search ............ 530/385
See application file for complete search history.

(56) References Cited

U.S. PATENT DOCUMENTS

| 5,028,588 | A |   | 7/1991  | Hoffman et al. |
| 5,428,007 | A | * | 6/1995  | Fischer et al. ............ 514/6 |
| 5,449,759 | A |   | 9/1995  | Hoffman et al. |
| 5,545,727 | A |   | 8/1996  | Hoffman et al. |
| 5,563,254 | A |   | 10/1996 | Hoffman et al. |
| 5,599,907 | A |   | 2/1997  | Anderson et al. |
| 5,665,869 | A |   | 9/1997  | Ryland et al. |
| 5,739,011 | A |   | 4/1998  | Anderson et al. |
| 5,798,227 | A |   | 8/1998  | Hoffman et al. |
| 5,801,019 | A |   | 9/1998  | Anderson et al. |
| 5,843,888 | A | * | 12/1998 | Ho et al. ............ 514/6 |
| 5,844,088 | A |   | 12/1998 | Hoffman et al. |
| 5,844,089 | A |   | 12/1998 | Hoffman et al. |
| 5,844,090 | A |   | 12/1998 | Anderson et al. |
| 5,942,488 | A |   | 8/1999  | Komiyama et al. |
| 6,022,849 | A | * | 2/2000  | Olson et al. ............ 514/6 |
| 6,114,505 | A | * | 9/2000  | Olson et al. ............ 530/385 |

FOREIGN PATENT DOCUMENTS

| WO | WO 95/14038 | 5/1995 |
| WO | WO 96/40920 | 12/1996 |
| WO | WO 97/23631 | 7/1997 |

OTHER PUBLICATIONS

Moore, E., et al., "Cooperativity in the Dissociation of Nitric Oxide from Hemoglobin*,"1976 *Journal of Biological Chemistry*, vol. 251, pp. 2788-2794.

Bonaventura, J., et al., "Hemoglobin Providence—Functional Consequences of Two Alterations of the 2,3-Diphosphoglycerate Binding Site at Position β82*," 1976 (*Journal of Biolological Chemistry*, vol. 251), pp. 7563-7571.

Doyle, M., et al., "Oxidation of Nitrogen Oxides by Bound Dioxygen in Hemoproteins,"1981 (*Journal of Inorganic Biochemistry*, vol. 14), pp. 351-358.

Fermi, G., et al., "The Crystal Structure of Human Deoxyhaemoglobin at 1-74 Å Resolution,"1984 *Journal of Molecular Biology*, vol. 175, pp. 159-174.

White, C., et al., "Toxicity of Human Hemoglobin Solution Infused into Rabbits," 1986 (*J. Lab. Clin. Med.*, vol. 108), pp. 121-131.

Nagai, K., et al. "Distal Residues in the Oxygen Binding Site of Haemoglobin Studied by Protein Engineering," 1987 (*Nature*, vol. 329), pp. 858-860.

Imai, K., et al. "Structural and Functional Consequences of Amino Acid Substitutions in Hemoglobin as Manifested in Natural and Artificial Mutants," 1989 (*Protein Seq. Data Anal.*, vol. 2), pp. 81-86.

Mitraki, A., et al. "Protein Folding Intermediates and Inclusion Body Formation,"1989 (*Bio/Technology*, vol. 7), pp. 690-697.

Mathews, A. J., et al., "The Effects of E7 and E11 Mutations on the Kinetics of Ligand Binding to R State Human Hemoglobin*," 1989 (*Journal of Biological Chemistry*, vol. 264), pp. 16573-16583.

Lin, S. H., et al. "Effect of the Distal Residues on the Vibrational Modes of the Fe-CO Bond in Hemoglobin Studied by Protein Engineering," 1990 (*Biochemistry*, vol. 29), pp. 5562-5571.

Mathews, A. J., et al. "The Assignment of Carbon Monoxide Association Rate Constants to the α and β Subunits in Native and Mutant Human Deoxyhemoglobin Tetramers*," 1991 (*Journal of Biological Chemistry*, vol. 266), pp. 21631-21639.

(Continued)

*Primary Examiner*—Karen Cochrane Carlson
(74) *Attorney, Agent, or Firm*—Senniger Powers

(57) ABSTRACT

The invention relates to novel recombinant hemoglobins having reduced nitric oxide scavenging and/or increased high soluble expression. The invention further relates to methods of increasing the soluble expression of recombinant hemoglobin by adding exogenous hemin in molar excess of the heme binding sites of recombinant hemoglobin.

6 Claims, 13 Drawing Sheets

OTHER PUBLICATIONS

Tame, J., et al. "Functional Role of the Distal Valine (E11) Residue of α Subunits in Human Haemoglobin," 1991 (*J. Mol. Biol.*, vol. 218), pp. 761-767.

Giardina, B., et al."Protein Engineering in Haemoglobin [letter]," 1992 (*Nature*, vol. 355), pp. 777-778.

Looker, D., et al.—"A Human Recombinant Haemoglobin Designed for Use as a Blood Substitute," 1992 (*Nature*, vol. 356), pp. 258-260.

Alayash, A., et al., "Nitric Oxide Binding to Human Ferrihemoglobins Cross-Linked Between Either α or β Subunits[1]," 1993 (*Archives of Biochemical Biophysics*, vol. 303), pp. 332-338.

Rooney, M., et al., "Hemodilution with Oxyhemoglobin—Mechanism of Oxygen Delivery and Its Superaugmentation with a Nitric Oxide Donor (Sodium Nitroprusside),"1993 (*Anesthesiology*, vol. 79), pp. 60-72.

Schultz, S., et al., "A Role for Endothelin and Nitric Oxide in the Pressor Response to Diaspirin Cross-Linked Hemoglobin,"1993 (*J. Lab. Clin. Med*, vol. 122), pp. 301-308.

Feldman, P., et al., "The Surprising Life of Nitric Oxide," 1993 (*Chem. Eng. News*, Dec.) pp. 26-38.

Fronticelli, C., et al., "The Dimer-Tetramer Equilibrium of Recombinant Hemoglobins. Stabilization of the $\alpha_1 \beta_2$ Interface by the Mutation β(Cys112→Gly) at the $\alpha_1 \beta_1$ Interface," 1994 (*Biophysical Chemistry*, vol. 51), pp. 53-57.

Thompson, A., et al., "Stroma-Free Hemoglobin Increases Blood Pressure and GFR in the Hypotensive Rat: Role of Nitric Acid,"1994 (*J. Appl. Physiol.*, vol. 77), pp. 2348-2354.

Hargrove, M.S., et al. "His64(E7)→Tyr Apomyoglobin as a Reagent for Measuring Rates of Hemin Dissociation*," 1994 (*J. Biol. Chem.*, vol. 269), pp. 4207-4214.

Looker, D., et al., "Expression of Recombinant Human Hemoglobin in *Escherichia coli*," 1994 (*Methods in Enzymolology*, vol. 231), pp. 364-374.

Fronticelli, C., et al. "Chloride Ion Independence of the Bohr Effect in a Mutant Human Hemoglobin β (V1M=H2deleted)*," 1994 (*Journal of Biological Chemistry*, vol. 269), pp. 23965-23969.

Lincoln, T.—"Protein Engineering. Hunting Haemoglobin [news; comment]," 1995 *Nature*, vol. 373, p. 196.

Alayash, A., et al., "Hemoglobin and Free Radicals: Implications for the Development of a Safe Blood Substitute," 1995 (*Mol. Med. Today*, vol. 1), pp. 122-127.

Carver & Kutlow, 1995, (*International Hemoglobin Information Center Variant List Hemoglobin*, vol. 19), pp. 37-149.

Militello, V., et al. "Dynamic Properties of Some β-Chain Mutant Hemoglobins,"1995 (*Proteins*, vol. 22), pp. 12-19.

Gould, S., et al., "Clinical Development of Human Polymerized Hemoglobin as a Blood Substitute,"1996 (*World Journal of Surgery*, vol. 20), pp. 1200-1207.

Eich, R. F., et al. "Mechanism of NO-Induced Oxidation of Myoglobin and Hemoglobin," 1996 (*Biochemistry*, vol. 35), pp. 6976-6983.

Pechik, I., et al. "Crystallographic, Molecular Modeling, and Biophysical Characterization of the Valine$^{\beta 67}$(E11)→Threonine Variant of Hemoglobin," 1996 (*Biochemistry*, vol. 35), pp. 1935-1945.

Sanders, K. E., et al. "Engineering and Design of Blood Substitutes," 1996 (*Current Opinion in Structural Biology*, vol. 6), pp. 534-540.

Kiger, L., et al. "Recombinant [Pheβ63] Hemoglobin Shows Rapid Oxidation of the β Chains and Low-Affinity, Non-Cooperative Oxygen Binding to the α Subunits,"1996 (*Eur. J. Biochem.*, vol. 243), pp. 365-373.

Cupane, A., et al."Modification of α-Chain or β-Chain Heme Pocket Polarity by Val(E11)→thr Substitution Has Different Effects on the Steric, Dynamic, and Functional Properties of Human Recombinant Hemoglobin. Deoxy Derivatives*" 1997 (*Journal of Biological Chemistry*, vol. 272), pp. 26271-26278.

Shen, T. J. , et al."Production of Human Normal Adult and Fetal Hemoglobins in *Escherichia Coli*," 1997 (*Protein Engineering*, vol. 10), pp. 1085-1097.

Sun, D. P., et al. "Contribution of Surface Histidyl Residues in the α-Chain to the Bohr Effect of Human Normal Adult Hemoglobin: Roles of Global Electrostatic Effects," 1997 (*Biochemistry*, vol. 36), pp. 6663-6673.

Netzer, W., et al., "Recombination of Protein Domains Facilitated by Co-Translational Folding in Eukaryotes," 1997 (*Nature*, vol. 388), pp. 343-349.

Olson, J., et al., "Protein Engineering Strategies for Designing More Stable Hemoglobin-Based Blood Substitutes," 1997 (*Art, Cells, Blood Subs. and Immob. Biotech.*, vol. 25), pp. 227-241.

Hargrove, M. S., et al. "Quaternary Structure Regulates Hemin Dissociation from Human Hemoglobin* [Published Erratum Appears in J. Biol Chem Sep. 19, 1997, 272(38):24096]," 1997 (*Journal of Biological Chemistry*, vol. 272), pp. 17385-17389.

Verderber, E., et al., "Role of the *hemA* Gene Product and δ-Aminolevulinic Acid in Regulation of *Escherichia coli* Heme Synthesis," 1997 (*Journal of Bacteriology*, vol. 179), pp. 4583-4590.

Weickert, M., et al., "Turnover of Recombinant Human Hemoglobin in *Escherichia coli* Occurs Rapidly for Insoluble and Slowly for Soluble Globin," 1997 (*Arch. Biochem. Biophys.*, vol. 348), pp. 337-346.

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
agcgaaggta ccgtccaggt t                                        21

<210> SEQ ID NO 2
<211> LENGTH: 22
<212> TYPE: DNA
<213> ORGANISM: Homo sapiens

<400> SEQUENCE: 2
cctgactccg gaagaaaaat cc                                       22
```

HEMOGLOBIN MUTANTS WITH INCREASED SOLUBLE EXPRESSION AND/OR REDUCED NITRIC OXIDE SCAVENGING

This application is a Divisional application of prior application No. 09/403,208, now U.S. Patent No. 6,455,676, filed Apr. 25, 2000, which was the National Stage of International Application No. PCT/US98/08861, filed May 1, 1998, which claims the benefit of U.S. Provisional Application No. 60/045,364, filed May 2, 1997 and U.S. Provisional Application No. 60/057,986, filed Sep. 5, 1997. The disclosures of these related applications are expressly incorporated herein by reference.

FIELD OF THE INVENTION

The invention relates to novel hemoglobin mutants having one or more desired functions, including reduced nitric oxide scavenging and increased soluble expression. The invention further relates to methods of increasing soluble expression of recombinant hemoglobin by the addition of excess heme.

BACKGROUND OF THE INVENTION

Hemoglobin (Hb) is the oxygen-carrying component of blood that circulates through the bloodstream inside small enucleate cells known as erythrocytes or red blood cells. It is a protein comprised of four associated polypeptide chains that bear prosthetic groups known as hemes. The structure of hemoglobin is well known and described in Bunn & Forget, eds., *Hemoglobin: Molecular, Genetic and Clinical Aspects* (W. B. Saunders Co., Philadelphia, Pa.: 1986) and Fermi & Perutz "Hemoglobin and Myoglobin," in Phillips and Richards, *Atlas of Molecular Structures in Biology* (Clarendon Press: 1981).

Expression of various recombinant hemoglobins containing naturally-occurring and non-naturally occurring globin mutants has been achieved. Such expression methods include individual globin expression as described, for example, in U.S. Pat. No. 5,028,588, and di-alpha globin expression created by joining two alpha globins with a glycine linker through genetic fusion coupled with expression of a single beta globin gene to produce a pseudotetrameric hemoglobin molecule as described in WO 90/13645 and Looker et al., *Nature* 356:258–260 (1992). Other modified recombinant hemoglobins are disclosed in PCT Publication WO 96/40920. Similar to other heterologous proteins expressed in *E. coli*, recombinant hemoglobins have N-terminal methionines, which in some recombinant hemoglobins replace the native N-terminal valines.

The process cost of producing recombinant hemoglobin is affected by the yield of soluble protein. Economic production of heterologous protein in *E.coli* is especially challenging when the protein must not only be soluble and functional, and it is also composed of multiple subunits as for recombinant hemoglobin. In addition, recombinant hemoglobins require the enhanced presence of essential co-factors (prosthetic groups) such as heme and flavins through supplementation or increased endogenous production. In *E.coli*, soluble accumulation of recombinant hemoglobin is limited by heme availability as indicated by the fact that without heme supplementation, addition of δ-ALA, a heme precursor, increases heme and protein accumulation. Consequently, methods of increasing soluble yield are highly desirable. However, prior to the present invention, the effect of mutations on soluble *E. coli* expression had not been studied nor were the determinants of soluble yield thoroughly understood. Thus, a need exists for methods of increasing soluble yield of recombinant hemoglobin.

A need also exists for methods of reducing scavenging of nitric oxide ("NO") by extracellular hemoglobin. Mild hypertension has sometimes been observed following administration of certain extracellular hemoglobin solutions. It is believed by many that the hypertension is due to depletion of nitric oxide ("NO") in the wall of the vasculature based in part on the known high affinity of deoxyhemoglobin for NO (Schultz et al., *J. Lab. Clin. Med.* 122: 301–308 (1993); Thompson et al., *J. Appl. Physiol.* 77:2348–2354 (1994); Rooney et al., *Anesthesiology* 79:60–72 (1993)). Extravasation of the hemoglobin into endothelial cells or interstitial spaces may cause significant consumption of NO (Gould et al., *World J. Sur.* 20: 1200–1207 (1996)). A recent study also suggests that the oxidative reaction of NO with the bound $O_2$ of oxyhemoglobin may be of greater significance in vivo than simple binding to the iron atom as reported in Eich et al., *Biochemistry* 35: 6976–6983 (1996). Eich et al. showed that steric hinderance introduced by substitution of amino acids adjacent to bound oxygen can markedly lower the rate of NO-induced oxidation.

Nitric oxide acts as a chemical messenger in the control of many important processes in vivo, including neurotransmission, inflammation, platelet aggregation, and regulation of gastrointestinal and vascular smooth muscle tone. The biological actions of nitric oxide are mediated by binding to and activation of soluble guanylyl cyclase, which initiates a biochemical cascade resulting in a variety of tissue-specific responses (Feldman et al., *Chem. Eng. News* Dec: 26–38 (1993)).

Elucidating the functions of nitric oxide has depended largely on inhibition of the NO-generating enzyme, nitric oxide synthase. Most conclusions about the effects of cell-free hemoglobin have been drawn based on experiments involving NO synthase inhibitors and/or NO donors.

While the rapid, high-affinity binding of nitric oxide to deoxyhemoglobin is well known, the importance of the oxidative reaction between NO and oxyhemoglobin is not as widely appreciated. In this reaction, the NO molecule does not bind to the heme, but reacts directly with the bound oxygen of the $HbO_2$ complex to form methemoglobin and nitrate (Doyle et al., *J. Inorg. Biochem.* 14: 351–358 (1981)). The chemistry is analogous to the rapid reaction of NO with free superoxide in solution (Huie et al., *Free Rad. Res. Comms.* 18: 195–199 (1993)). Both the heme iron and nitric oxide become oxidized by the bound oxygen atoms, and the reaction occurs so rapidly that no replacement of $O_2$ by NO is observed (Eich et al., supra.).

Since nitric oxide is produced and consumed on a continuous basis, there is a natural turnover of NO in vivo. When a cell-free hemoglobin is administered, the balance between NO production and consumption is altered by reactions with hemoglobin. The most relevant parameter for NO scavenging by oxyhemoglobin is the rate of reaction with NO, not the position of the Hb allosteric (R/T) equilibrium. The oxidative reaction is irreversible, and NO binding to deoxyhemoglobin is effectively irreversible on physiologic timescales since the half-life for dissociation of nitrosylhemoglobin is 5–6 hours (Moore et al., *J. Biol. Chem.* 251: 2788–2794 (1976).

Once an NO molecule reacts with oxyhemoglobin or deoxyhemoglobin, it is eliminated from the pool of signal molecules causing certain adverse conditions. For example, hemoglobin can bind nitric oxide causing the prevention of vascular relaxation and potentially leading to hypertension that is sometimes observed after administration of certain extracellular hemoglobin solutions. In addition, the ability of NO to oxidize oxyhemoglobin producing peroxynitrite and methemoglobin could also lower free concentrations of NO and lead to hypertension.

Nitric oxide is also needed to mediate certain inflammatory responses. For example, nitric oxide produced by the endothelium inhibits platelet aggregation. Consequently, as nitric oxide is bound by cell-free hemoglobin, platelet aggregation may be increased. As platelets aggregate, they release potent vasoconstrictor compounds such as thromboxane $A_2$ and serotinin. These compounds may act synergistically with the reduced nitric oxide levels caused by hemoglobin scavenging resulting in an significant vasoconstriction.

In addition to inhibiting platelet aggregation, nitric oxide also inhibits neutrophil attachment to cell walls, which in turn can lead to cell wall damage. Endothelial cell wall damage has been observed with the infusion of certain hemoglobin solutions (White et al., *J. Lab. Clin. Med.* 108:121–181 (1986)).

Accordingly, a need exists for new hemoglobin mutants with decreased NO-scavenging while still functioning as an effective oxygen carrying agent. The present invention satisfies this need as well as the need for increased soluble yield of recombinant hemoglobin.

SUMMARY OF THE INVENTION

The invention relates to hemoglobin mutations that confer certain desired functions, such as increased yield of soluble Hb and reduced NO scavenging. The hemoglobin mutants can be designed to include these functions separately or in combination.

Therefore, in one aspect, the invention is directed to introducing a mutation into one or more beta and/or alpha subunits of recombinant hemoglobin to increase the yield of soluble recombinant hemoglobin compared to the unmodified protein. The methods are accomplished by:
(a) incorporating into a host cell a vector containing a gene encoding a globin having at least one mutation that directs high soluble expression of the recombinant hemoglobin;
(b) inducing the host cell to express soluble recombinant hemoglobin; and
(c) purifying the soluble recombinant hemoglobin.

Useful mutations in the beta subunit include D73I, D73M, D73E, D73T, D73Y, K82D, K82E, K82G, K82P, K82Q, K82S, K82N, N102A and N102V.

Alternatively, or in combination with the above method, high expression levels of soluble hemoglobin can be obtained by adding excess henin, preferably at least a 2.5-fold molar excess of hemin.

In another aspect, the invention further relates to novel hemoglobin mutants having reduced rates of reaction with nitric oxide. Mutations in the alpha subunit having desired rates of reaction include:
E11(Val→Leu)
B10(Leu→Trp)+E7(His→Gln)
B10(Leu→Trp)+E11(Val→Phe)
B10(Leu→Trp)+E11(Val→Leu)+G8(Leu→Trp)
B10(Leu→Trp)+E11(Val→Phe)+G8(Leu→Trp)
B10(Leu→Trp)+E11(Val→Phe)+G8(Leu→Ile)
B10(Leu→Trp)+E7(His→Gln)+E11(Val→Leu)+G8 (Leu→Trp)
B10(Leu→Trp)+E11(Val→Trp)+G8(Leu→Trp)
E11(Val→Leu)+G8(Leu→Phe)
E11(Val→Leu)+G8(Leu→Trp)
E11(Met→Phe or Trp)
G12(Leu→Phe or Trp), and
B14(Phe→Trp)

Mutations in the beta subunit having desired rates of reaction include:
E11(Val→Leu)
B13(Leu→Phe or Trp)
G12(Leu→Phe or Trp)
B14(Leu→Phe or Trp)
G8(Leu→Phe)+G12 (Leu→Trp)
E11(Val→Leu)+G8(Leu→Trp)
E11(Val→Trp)+G8(Leu→Met)
E11(Val→Leu)+G8(Leu→Phe)
E11(Val→Leu)+G8(Leu→Met)
E11(Val→Phe)+G8(Leu→Ile)
E11(Val→Phe)+G8(Leu→Phe)
E11(Val→Phe)+G8(Leu→Trp)
E11(Val→Phe)+G8(Leu→Met)
E11(Val→Met)+G8(Leu→Trp)
E11(Val→Met)+G8(Leu→Trp)+E7(His→Gln)
E11(Val→Trp)+G8(Leu→Ile)
E7(His→Gln)
E7(His→Gln)+E11(Val→Trp)
E7(His→Gln)+E11(Val→Leu)
E7(His→Gln)+E11(Val→Phe)
E7(His→Gln)+E11(Val→Phe)+G8(Leu→Phe or Trp)
E7(His→Gln)+E11(Val→Leu or Trp)+G8(Leu→Phe or Trp)
E7(His→Phe)
E11(Val→Trp or Phe)+G12 (Leu→Trp or Met)
E11(Val→Trp or Phe)+B13(Leu→Trp or Met)
B10(Leu→Trp)+B13(Leu→Trp or Met)
B10(Leu→Phe)+B13(Leu→Trp)
B10(Leu→Trp or Phe)+G12 (Leu→Trp)
B10(Leu→Phe)+G12(Leu→Met)
E11(Val→Phe, Met or Leu)+G8(Leu→Trp, Met or Phe)
G8(Leu→Phe)+G12(Leu→Trp)
G8(Leu→Trp)+G12(Leu→Trp or Met), and
G8(Leu→Trp)+B13(Leu→Trp or Met)

Preferably, such mutations have rate constants for reaction of NO with oxyhemoglobin of less than 25 $\mu M^{-1}s^{-1}$, more preferably between 12 and 15 $\mu M^{-1}s^{-1}$, and most preferably less than 5 $\mu M^{-1}s^{-1}$.

DETAILED DESCRIPTION OF THE INVENTION

Figure 1:
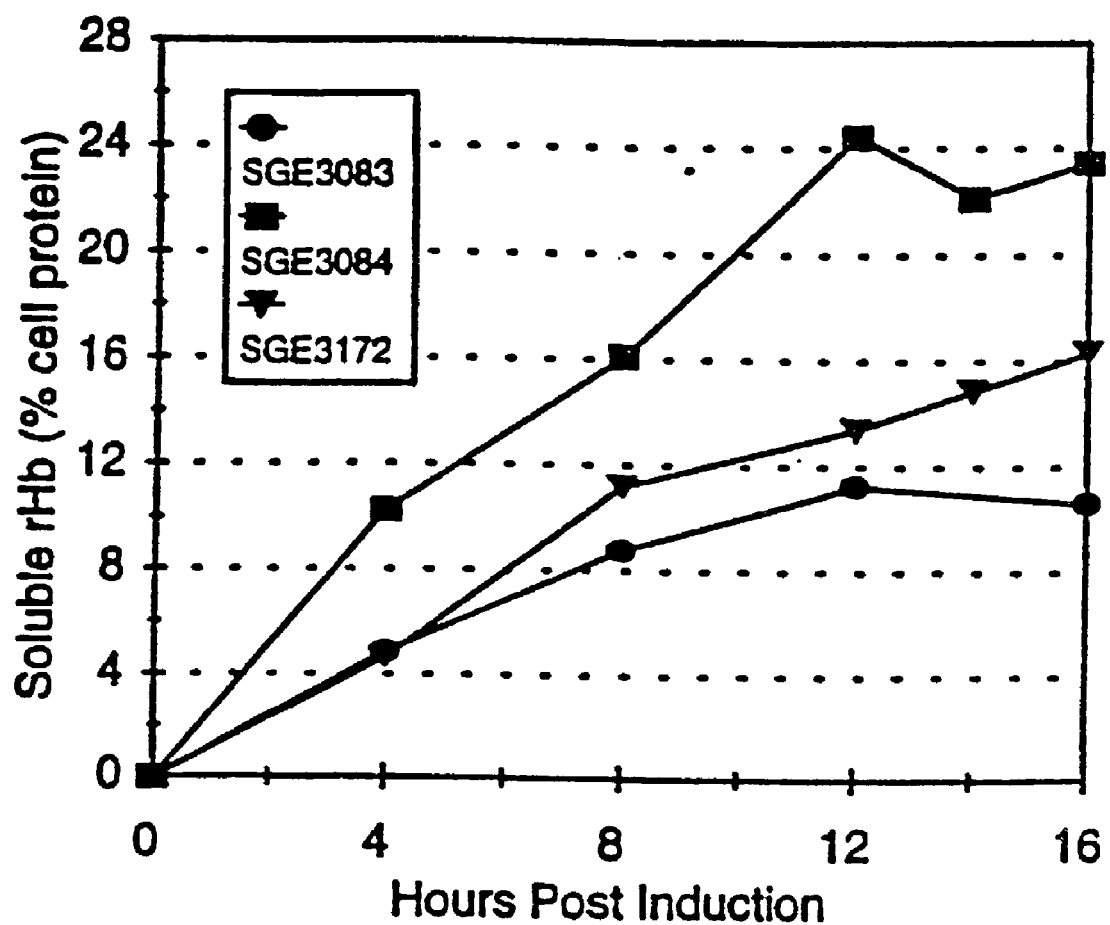
FIG. 1 shows the accumulation of solube hemoglobin (Hb) for three variants of soluble rHb with a di-αK158C mutation up to 16 hours post induction. Theses are: rHb di-α K158C/βN108K (SGE3083; circles), rHb di-α K158C/βK82D (SGE3084; squares) and ), rHb di-α K158C/βN108K,K82D (SGE3172; triangles) accumulation for 16 hours after induction. Heme supplementation was made at 0, 3, 6, 9 and 12 ours post induction to a final concentration of 0.63 mM hemin. Each symbol represents the average from four fermentations except for SGE3083 data, which are the average of two.

The invention generally relates to hemoglobin mutations that, either separately or in combination, confer increased soluble expression or reduced NO scavenging. Thus, in one aspect, the invention relates to methods of producing high soluble expression of recombinant hemoglobin in a host cell. It has now been discovered that high soluble expression of recombinant hemoglobin ("rHb") can be obtained by introducing certain mutations into the globin subunits separately or in combination with the addition of excess heme. As used herein, the term "high soluble expression" means soluble expression levels of recombinant hemoglobin that are greater than expression levels obtained without an alteration that improves soluble expression and/or the addition of at least about a 2.5-fold molar excess of hemin. Preferably, high soluble expression levels include an increase of at least 5%, more preferably at least 10%, and even more preferably at least 50%.

The methods of the present invention are generally accomplished by:

(a) incorporating into the host cell a gene encoding a globin having at least one mutation that directs high soluble expression of the recombinant hemoglobin;

(b) culturing the host cell to express soluble recombinant hemoglobin with or without the addition of excess hemin; and (c) purifying the soluble recombinant hemoglobin.

In one embodiment of the invention, a desired hemoglobin or hemoglobin-like molecule can be altered or modified to contain one or more mutations to enhance its soluble yield. Preferably, the non-modified hemoglobin is human hemoglobin. However, hemoglobin from other species are also candidates for increased soluble expression including, for example, primate, bovine, fowl, fish, shark and other invertebrates such as *Artemia*, earthworm, sea lamprey, mollusc and marine bloodworms.

Suitable recombinant hemolgobin candidates for increased soluble expression include wholly or partially wildtype hemoglobins. In another embodiment, the recombinant hemoglobin can be naturally or non-naturally occurring hemoglobin mutants containing mutations in the alpha and/or beta globins as described, for example, in U.S. Pat. No. 5,028,588, incorporated herein by reference. Such mutations can confer other desired characteristics in addition to enhancement of soluble expression, such as high or low oxygen affinity or cooperativity, enhancements in stability and assembly rates, decreased heme loss rates or autooxidation rates, or resistance to proteolytic degradation and aggregation.

Other recombinant hemoglobins suitable for increased soluble expression include the hemoglobin-like molecules (pseudotetramers) disclosed in U.S. Pat. Nos. 5,449,759 and 5,545,727, both incorporated herein by reference. The mutant and modified hemoglobins described in U.S. Pat. No.

5,599,907 and WO 96/40920 and WO 97/23631, all incorporated herein by reference, are also suitable target proteins for enhanced soluble expression.

Mutations that direct high soluble expression can appear in the alpha and/or beta globin. Although not wishing to be bound by any particular theory, it is believed a mutation that stabilizes hemoglobin or increases assembly or folding rates can also lead to improved soluble yield. Accordingly, mutations that stabilize alpha helices, such as alanine substitutions, or that increase hydrophobic core packing, for example, by substituting internal hydrophilic amino acids with hydrophobic amino acids, are generally useful mutations for the methods of the present invention. Other generally useful mutations include: (1) those that stabilize the $alpha_1 beta_2$ interface, such as naturally occurring mutant Hb Kansas; (2) substitutions with charged amino acids at surface sites, such as the naturally occurring mutant Hb Vancouver; and (3) substitutions with polar or charged amino acids at the diphosphoglycerate-binding site. Amino acid substitutions at beta surface site D73 that have a volume between that of aspartate and lysine are also generally useful mutations. Such amino acids include aspartate, valine, asparagine, leucine, isoleucine, glutamine, methionine, glutamate, histidine and lysine.

For example, the naturally occurring Providence mutant occurs at a key residue in the DPG binding cleft (K82D or Lys82→Asp) between the two beta subunits in the hemoglobin tetramer. This anion binding cleft is lined with at least six positively charged residues, three from each beta globin (His2, His143, and Lys82). In the absence of DPG or inositol hexaphosphate, such as during accumulation of rHbs in *E. coli*, an electrostatic repulsion between these residues may destabilize or even partially denature the beta globin structure. Substitution of the normally occurring positively charged lysine by a negatively charged aspartate introduces a counterion to the DPG pocket, which may form an electrostatic interaction with His143, is likely to stabilize the beta chain. This substitution could account for the improved soluble accumulation of rHb9.1 versus rHb0.1, which contains the wild type lysine at position 82. The charge substitution may also increase the rate of hemoglobin assembly by reducing the electrostatic repulsion in this region. Differences in accumulation of stable hemoglobin variants in humans appears largely correlated with differences in subunit assembly rates.

It is likely that the same Lys82→Asp (Providence) substitution could stabilize and improve soluble accumulation of other recombinant hemoglobin molecules, since all are typically expressed without DPG present. This was observed with a di-α mutant rHb, Lys158→Cys, in which Providence ("Prov") more than doubled soluble accumulation. The addition of the Providence mutation to rHb 1.1, to create rHb9+1.1, achieved a greater than 2-fold increase in soluble expression, rescuing the Presbyterian mutant by restoring the soluble expression to wild type levels. In addition to improving soluble accumulation, rHb variants also increased total globin accumulation implying that the soluble hemoglobin is more stable than the insoluble protein. This result is consistent with pulse chase experiments in which insoluble globin was observed to have a much shorter half life than soluble globin. Thus the greater amount of globin maintained in soluble form, the greater the total accumulation expected, since the insoluble globin is more rapidly removed.

Useful beta mutations for high soluble expression include, for example, D73I, D73M, D73E, D73T, D73Y, K82D, K82E, K82G, K82P, K82Q, K82S, K82N, N102A and N102V. A number of these variants have soluble expression yields greater than the corresponding recombinant hemoglobins with the wild-type amino acid at the target mutation site. The nomenclature used in referring to a particular mutation first identifies the wild-type amino acid, followed by the residue number and finally the substitute amino acid. For example, D73I means that aspartate has been substituted with isoleucine at residue number 73.

Combinations of mutations are also useful for high soluble expression. Examples of useful beta globin mutant combinations are listed in Tables 1 and 2. In Table 2, certain strains and their descriptions are listed to provide information about the basic strains that can be altered with useful beta mutations. For example, SGE3011 is the basic strain used to produce SGE3010 in addition to several others.

TABLE 1

Beta Mutant Combinations

Providence + Tilburg
Providence + Vancouver
SGE3011 beta (V67W) + D73E
SGE3011 beta (V67W) + D73I
SGE3011 beta (V67W) + D73Y (Vancouver)
SGE3011 beta (V67W) + D73E + K82D (Providence)
SGE3011 beta (V67W) + D73I + K82D (Providence)
SGE3011 beta (V67W) + D73Y (Vancouver) + K82D (Providence)
SGE3011 beta (V67W) + K82E
SGE3011 beta (V67W) + K82G

TABLE 2

| Strain | Description |
| --- | --- |
| SGE3004 | diαV62L/βV67F |
| SGE3005 | 3004 + St. Mande |
| SGE3263 | 3004 + Providence + Presbyterian |
| SGE3173 | di-diα 3004 |
| SGE2821 | diαL29F, H58Q/βL106W |
| SGE1737 | 2821 + Presbyterian |
| SGE3006 | 2821 + Prov + St. Mande |
| SGE3007 | 2821 + Prov + Pres |
| SGE2822 | di-diα 2821 |
| SGE1738 | 2822 + Pres |
| SGE3008 | 2822 + Prov + St. Mande |
| SGE3009 | 2822 + Prov + Pres |
| SGE3001 | diαL29F/βV67W |
| SGE1728 | 3001 + Pres |
| SGE1729 | 3001 + Prov |
|  | di-diα 3001 |
| SGE3011 | diαL29W, H58Q/βV67W |
| SGE3010 | 3011 + Prov |
| SGE2966 | 3011 + Pres |
| SGE2968 | 3011 + Prov + Pres |
| SGE2967 | 3011 + St. Mande |
| SGE2963 | di-diα 3011 |
| SGE2971 | di-diα 3011 + Prov |
| SGE2969 | di-diα 3011 + Pres |
| SGE2972 | di-diα 3011 + Prov + Pres |
| SGE2970 | di-diα 3011 + St. Mande |
| SGE3012 | diαL29W, H58Q/βL106W |

The present invention further provides novel DNA sequences that encode the desired mutations that enhance soluble expression, some of which are identified in Table 16. For example, DNA that ultimately results in the Providence mutation is K82N, but this residue undergoes hydrolysis to yield K82D in vivo. Therefore, DNA directly encoding for aspartate is novel.

In general, those skilled in the art can construct genes encoding a mutant globin having at least one mutation that directs high soluble expression of the recombinant hemoglobin by techniques well-known in the art, including by complete DNA synthesis or by standard recombinant DNA methods (see, for example., Sambrook, et al., *Molecular Cloning: A Laboratory Manual*, 2$^{nd}$ ed. Cold Spring Harbor Laboratory Press, Cold Spring Harbor, N.Y. (1989)). Methods for incorporating the desired mutations are well known in the art and include, for example, site-directed mutagenesis. Random mutagenesis is also useful for generating a number of mutants at a particular site. Other recombinant techniques are also known, such as those described in U.S. Pat. No. 5,028,588, U.S. Pat. No. 5,545,727, U.S. Pat. No. 5,599,907, PCT Publications WO 96/40920 and WO 97/04110, all incorporated herein by reference.

The genes can be used to construct plasmids that are inserted into appropriate host cells according to conventional methods or as described in WO 96/40920, incorporated herein by reference. Any suitable host cell can be used to express the novel polypeptides. Suitable host cells include, for example, bacteria, yeast, mammalian, plants and insect cells and transgeneic animals. *E. coli* cells are particularly useful for expressing desired recombinant hemoglobin.

The transformed host cell is then cultured or fermented until soluble hemoglobin is harvested for purification. Purification of the soluble fraction can be accomplished using the methods described in WO 95/14038, incorporated herein by reference, or by following the guidance provided in the Examples below.

In a further embodiment of the invention, excess hemin can be added to obtain high soluble expression of recombinant hemoglobin. As used herein, "excess heme" means at least a 2.5-fold molar excess of hemin to heme binding sites in hemoglobin.

Measurements of the insoluble protein content in fermentations yielded evidence that reduction in soluble hemoglobin was due to conversion into insoluble globin. Loss of heme is a mechanism for turnover of soluble hemoglobin into insoluble globins that has been well-characterized as described in Mitraki & King, *Bio/Tch.*, 7:690–697 (1989). The rate of turnover was consistent with an 11 hour half-life of rHb1.1 in *E. coli* flask cultures (Weickert & Curry, *Arch. Biochem. Biophys.*, 348:337–346 (1997)), raising the possibility that when heme became limiting (dropped below a required stoichiometric level), soluble accumulation ceased, and turnover of rHb was driven primarily by heme loss, followed by insoluble aggregation.

Many unstable mutant human Hbs found in vivo in inclusion bodies contain heme, as do in vitro heat precipitated forms of mutant Hbs (Rachmilewitz, *Seminars in Hematology*, 11:441–462 (1974)). Heme may stabilize some globin conformations even in insoluble aggregates, and its absence from one or more of the four hemoglobin subunits, may lead to insolubility and rapid turnover of the subunits (Weickert & Curry, supra). Although globin can accept heme before it is released from the ribosome in eukaryotic cell free translation systems, it is unclear whether this occurs in bacteria. Unlike in eukaryotes, globin probably cannot complete folding to its native configuration until its release from the ribosome in *E. coli* (Netzer & Hartl, *Nature.* 388: 343–349 (1997)). Therefore, without heme, apo-globin can be likened to a trapped folding intermediate.

In the experiments described in the Examples below, the expression strains and plasmids were identical, as were the fermentation and induction conditions. Therefore, approximately the same amount of protein synthesis occurred for each rHb variant. No significant differences in cell growth were observed suggesting that rHb variants did not have different toxic effects on the cells, which could have accounted for the differences in the percent of the soluble protein accumulating as soluble rHb.

The extracellular heme concentration was manipulated to study the influence on intracellular heme concentration. The use of identical expression strains imposes the same heme transport (diffusion) and biosynthetic capacity for cells expressing each rHb variant. The *E. coli* strains were sufficiently heme permeable to allow a heme protein, rHb9.1, to accumulate to almost 40% of the soluble protein in the cell. Since very high soluble expression of rHbs requires more than a 2.5-fold molar excess of heme, this excess is believed to be required for sufficient diffusion across the cell membrane to maintain an intracellular heme concentration high enough to drive the bimolecular reaction of heme with globin. Fermentations not supplemented with heme accumulated only about 12–15% of the soluble rHb0.1 achieved when hemin was supplemented, indicating that biosynthesis of heme contributes little to the soluble globin and therefore to the heme pool within the cell.

In another aspect, the present invention also relates to novel mutant hemoglobins that have significantly reduced rates of reaction with nitric oxide or NO scavenging. As such, the mutant hemoglobins of this aspect of the present invention are also referred to herein as "NO mutants."

The NO mutants have one or more mutations in or around the heme pocket. Heme is an iron-containing porphyrin that serves as a prosthetic group in proteins such as hemoglobin, myoglobin and the cytochromes. In hemoglobin, the heme appears in a cleft between the E and F helices in the globin subunits. The heme iron is linked covalently to the imidazole nitrogen of the, "proximal" F8 histidine, while the distal E7 histidine and E11 valine appear near the access of oxygen to the heme pocket. The residues of the heme pocket include those residues that are on a nearest atom-to-nearest atom basis within 6 angstroms, and preferably within 4 angstroms, of the heme moiety (Fermi, et al. (1984) J. Mol. Biol. 175: 159–174). For alpha globin, the heme pocket residues include:

| First shell | Second Shell |
|---|---|
| Distal residues: | |
| B10 Leu | B13 Met |
| CE1 Phe | CE3 His |
| E7 His | CE4 Phe |
| E11 Val | E10 Lys |
| G8 Leu | E14 Ala |
| | G12 Leu |
| | B14 Phe |
| Proximal residues: | |
| F8 His | C7 Tyr |
| | F4 Leu |
| | F7 Leu |
| | FG3 Leu |
| | FG5 Val |
| | G4 Asn |
| | G5 Phe |
| | H15 Val |
| | H19 Leu | and for beta globin:

| First shell | Second Shell |
|---|---|
| Distal residues: | |
| B10 Leu | B13 Leu |
| CD1 Phe | CD3 Ser |
| E7 His | B14 Leu |
| E11 Val | CD4 Phe |
| G8 Leu | E10 Lys |
| | E14 Ala |
| | G12 Leu |
| Proximal residues: | |
| F8 His | C7 Phe |
| | F4 Leu |
| | F7 Leu |
| | FG3 Leu |
| | FG5 Val |
| | G4 Asn |
| | G5 Phe |
| | G12 Leu |
| | H15 Val |
| | H19 Leu |

The first shell residues are those residues in close or direct contact with the heme iron atom and/or the bound ligand, while second shell residues are those amino acids which are not in direct contact with the heme or the bound ligand, but are in direct contact with first shell residues. The term "heme pocket residues" include these first and second shell residues.

Various terms are used herein in describing this aspect of the present invention. Unless defined otherwise, all technical and scientific terms used herein have the same meaning as commonly understood by those skilled in the art.

For the purposes of this invention, "naturally occurring human hemoglobin," "native hemoglobin," "wild type hemoglobin" or "conventional hemoglobin" refer to human hemoglobin $A_o$ whose alpha and beta globin amino acid sequences are given in FIG. 1 of U.S. Pat. No. 5,028,588, incorporated herein by reference. Note that it is conventional to identify the helical segments of the globin subunits by letters, for example, the proximal histidine of the alpha chain or the beta chain is termed F8 (residue 8 of helix F). The non-helical segments are identified by letter pairs, indicating which helical segments they connect, for example, non-helical segment BC connects helix B and helix C. The helical notation and corresponding amino acids for alpha and beta globin are shown in Table 4 of U.S. Pat. No. 5,028,588, incorporated herein by reference.

"Recombinant hemoglobin" means hemoglobin, whether native or mutant, comprising alpha-like globin proteins and/or beta-like globin proteins, at least one of which is obtained by expression of a globin gene carried by a recombinant DNA molecule in a cell other than the cell in which that hemoglobin gene and/or hemoglobin protein is naturally found. In other words, the hemoglobin gene is heterologous to the host in which it is expressed. For example, the expression of any human hemoglobin gene in any cell other than a human blood cell would be considered to be a recombinant hemoglobin.

As used herein, an "alpha globin" has at least about 75% sequence identity with native human alpha globin. However, a polypeptide of lesser sequence identity may still be considered substantially homologous with native human alpha globin, and thus may be an alpha globin, if it has a greater sequence identity than would be expected from chance and also has the characteristic higher structure of native human alpha globin and similar biological activity. Likewise, a "beta globin" has at least about 75% sequence identity with native human beta globin. However, a polypeptide of lesser sequence identity may still be considered substantially homologous with native human beta globin, and thus may be a beta globin, if it has a greater sequence identity than would be expected from chance and also has the characteristic higher structure of native human beta globin and similar biological activity.

"Liganded hemoglobin" means hemoglobin to which a ligand is bound at the heme groups. Common preferred ligands include, but are not limited to $O_2$, CO, NO and the like.

"Oxyhemoglobin" means hemoglobin in which an oxygen molecule is bound to the functional oxygen binding sites in each subunit.

"Deoxyhemoglobin" or "unliganded hemoglobin" means any hemoglobin to which no ligand is bound to the alpha globin, the beta globin, and/or any functional heme prosthetic group.

"Methemoglobin" or "oxidized hemoglobin" means any hemoglobin in which the iron has been oxidized to the ferric state.

"R-state hemoglobin" is the high affinity state of hemoglobin and is the dominant form of hemoglobin when a ligand is bound at the heme pockets. The ligand is typically oxygen, thus this state is known as the "oxy" or "R" (for relaxed) state. In the R state, intersubunit distances are increased relative to the distances in T-state hemoglobin.

"T-state hemoglobin" is the low affinity state of hemoglobin and is the dominant form of hemoglobin when it is deoxygenated ("deoxy", or "T" for "tense").

"Heme pocket" means that pocket formed around the heme of each globin subunit described by the surrounding residues and is meant to include residues within about 6 Å of the heme moiety and as described above.

"Distal heme pocket" means that portion of the heme pocket above the plane of the heme that contains the free coordination site of the iron where ligand molecules can combine reversibly with the iron atom and which contains such residues as histidine E7 and valine E11. Likewise, the proximal side of the heme pocket is described by those residues below the plane of the heme and contains such residues as the proximal histidine at position F8.

"Oxidation" means the oxidation of the iron in the heme of any or all of the subunits making up the hemoglobin tetramer from the ferrous ($Fe^{+2}$) to the ferric form ($Fe^{+3}$). Autooxidation occurs spontaneously without the addition of exogenous oxidants, however oxidation can be induced by the presence of exogenous oxidizing agents, most notably NO and hydrogen peroxide.

"Mutations" are substitutions, deletions or additions of one or more amino acids to the amino acid sequence that constitutes naturally occurring human hemoglobin.

"Affinity" refers to the equilibrium binding of a ligand to hemoglobin, and is described by the thermodynamic equilibrium constant, Keq. Affinity is the ratio of the ligand association rate and the hemoglobin-ligand dissociation rate, and thus changes in association rate, dissociation rate or both can lead to changes in ligand affinity.

"Altered affinity" means the affinity of a recombinant hemoglobin for a gaseous ligand that is at least 10% different from the affinity of naturally occurring human hemoglobin for that same gaseous ligand under the same measurement conditions.

In designing the NO mutants of the present invention, two independent protein engineering strategies were used to vary oxygen affinities and rate of reacktion with nitric acid: (1) manipulation of the intrinsic kinetics and affinities of NO and $O_2$, respectively, by making novel substitutions in the distal pockets of the subunits, and (2) adjustment of the position of the allosteric R/T equilibrium with mutations at key points away from the heme groups as described in Olson et al., *Art. Cells. Blood Subs., and Immob. Biotech.* 25: 227–241 (1997). Changes in hemoglobin allostery are specific for oxygen binding kinetics and affinity, while the R/T equilibrium has no effect on NO scavenging. The distal pocket substitutions affect entry and exit rates of NO and $O_2$ by varying steric hindrance and hydrogen bonding (Olson et al., supra.).

Thus, the general strategy for identifying NO mutants of the present invention is set forth as follows:

a) making mutations that cause one or more amino acid substitutions in the distal heme pockets of ax and P globin subunits;

b) incorporating DNA fragments containing these mutations into a suitable expression vector then introducing this vector into an appropriate host cell;

c) culturing the host cell, followed by a screening assay (e.g. ELISA) with antibodies to hemoglobin, to identify host cells expressing soluble hemoglobin;

d) culturing the host cell to express soluble hemoglobin followed by purification of the hemoglobin;

e) conducting in vitro testing to verify the decrease in NO-scavenging activity and retention of oxygen delivery as needed.

f) selecting the proper ax mutations to pair with the proper D mutations;

g) as needed, selecting other mutations to adjust the $P_{50}$ or rate of $O_2$ dissociation; and h) in vivo testing for $O_2$ delivery and hemodynamic data.

In following this strategy, mutant alpha subunits were first paired with wild-type beta subunits and vice versa. Additional mutants formed by combination of mutations in the alpha and beta globins were also constructed.

Any of the mutations described herein can be accomplished by a number of methods that are known in the art. Mutations can be made at the codon level by alteration of the nucleotide sequence that codes for a given amino acid. Substitution of an amino acid at any given position in a protein can be achieved by altering the codon for that particular amino acid. This substitution can be accomplished by site directed mutagenesis using, for example: (1) the Amersham technique (Amersham mutagenesis kit, Amersham, Inc., Cleveland, Ohio) based on the methods of Taylor et al., Nucl. Acids Res. (1985) 13: 8749–8764; Taylor et al., (1985) Nucl. Acids Res. 13: 8764–8785; Nakamaye and Eckstein, (1986) Nucl. Acids Res. 14: 9679–9698; and Dente et al., in *DNA Cloning*, Glover, Ed., IRL Press (1985) pages 791–802, (2), the Promega kit (Promega Inc., Madison, Wis.) or (3) the Biorad kit (Biorad Inc., Richmond, Calif.), based on the methods of Kunkel, (1985) Proc. Natl. Acad. Sci. USA 82: 488; Kunkel et al., (1987) Meth. Enzymol. 154: 367; Kunkel, U.S. Pat. No. 4,873,192. It can also be accomplished by other commercially available or non-commercial means which incorporate the technique of site-directed mutagenesis using mutant oligonucleotides to achieve mutagenesis or as described in the Examples below.

Site directed mutagenesis can also be accomplished using PCR based mutagenesis such as that described in Zhengbin et al., pages 205–207 in *PCR Methods and Applications, Cold Spring Harbor Laboratory Press*, New York (1992); Jones and Howard, (1990) *BioTechniques* 8(2):178 (1990); Jones and Howard, *BioTechniques* 10: 62–66 (1991), or as described in the Examples below. Site directed mutagenesis can also be accomplished using cassette mutagenesis with techniques that are known to those of skill in the art.

Any suitable host cell can be transformed with a plasmid containing the desired mutation(s) by methods known to those skilled in the art or as described in the Examples below. Suitable host cells include, for example, bacterial. yeast, plant, mammalian and insect cells. *E. coli* cells are particularly useful for expressing the novel mutant hemoglobins. Preferably, when multiple subunits are expressed in bacteria, it is desirable, but not required, that the subunits be co-expressed in the same cell polycistronically as described in WO 93/09143. It is preferable in *E. coli* to use a single promoter to drive the expression of the genes encoding the desired proteins.

The reaction of NO with oxyhemoglobin forms of the mutants often yielded biphasic reaction timecourses due to different reactivities of the two subunit types in the hemoglobin tetramer. Fitting these reaction timecourses to a two-exponential function yielded the reaction rates of both the wild-type and mutant subunits. By repeating this process for a large number of mutant constructs, a number of mutants in each subunit type were identified exhibiting a wide range of rate constants for NO reactivity ($k'_{NO,ox}$) were obtained. After purifying and screening the large number of mutants, the following alpha and beta globin mutants and combinations thereof were identified as having reduced NO reactivity compared to conventional hemoglobin:

α Globin Mutations:
E11(Val→Leu)
E11(Val→Leu)+E7(His→Gln)
E11(Val→Phe or Trp)+E7(His→Gln)
E11(Val→Phe or Trp or Leu)+E7(His→Gln)+G8(Leu→Phe or Trp)
B10(Leu→Trp)+E7(His→Gln)
B10(Leu→Trp)+E11(Val→Phe)
B10(Leu→Trp)+E11(Val→Trp)
B10(Leu→Trp)+E11(Val→Leu)+G8(Leu→Trp)
B10(Leu→Trp)+E11(Val→Leu)+G8(Leu→Phe)
B10(Leu→Trp)+E11(Val→Phe)+G8(Leu→Trp)
B10(Leu→Trp)+E11(Val→Phe)+G8(Leu→Ile)
B10(Leu→Trp)+E7(His→Gln)+E11(Val→Leu)+G8(Leu→Trp)
B10(Leu→Trp)+E11(Val→Trp)+G8(Leu→Trp)
E11(Val4Leu)+G8(Leu→Phe)
E11(Val→Leu)+G8(Leu→Trp)
B13(Met→Phe or Trp)
G12(Leu→Phe or Trp)
B14(Phe→Trp)

βGlobin Mutations:
E11(Val→Leu)
B13(Leu→Phe or Trp)
G12(Leu→Phe or Trp)
B14(Leu→4Phe or Trp)
G8(Leu→Phe)+G12 (Leu→Trp)
E11(Val→Leu)+G8(Leu→Trp)
E11(Val→Trp)+G8(Leu→Met)
E11(Val4Leu)+G8(Leu→Phe)
E11(Val→Leu)+G8(Leu→Met)
E11(Val→Phe)+G8(Leu→Ile)
E11(Val→Phe)+G8(Leu→Phe)
E11(Val→Phe)+G8(Leu→Trp)
E11(Val→Phe)+G8(Leu→Met)
E11(Val→Met)+G8(Leu→Trp)

E11(Val→Met)+G8(Leu→Trp)+E7(His→Gln)
E11(Val→Trp)+G8(Leu→Ile)
E7(His→Gln)
E7(His→Gln)+E11(Val→Trp)
E7(His→4Gln)+E11(Val→Leu)
E7(His→Gln)+E11(Val→Phe)
E7(His→Gln)+E11(Val→Phe)+G8(Leu→Phe or Trp)
E7(His→Gln)+E11(Val→Leu or Trp)+G8(Leu→Phe or Trp)
E7(His→Phe)
E11(Val→Trp or Phe)+G12(Leu→Trp or Met)
E11 (Val→Trp or Phe)+B13(Leu→Trp or Met)
B10(Leu→Trp)+B13(Leu→Trp or Met)
B10(Leu→Phe)+B13(Leu→Trp)
B10(Leu→Trp or Phe)+G12(Leu→Trp)
B10(Leu→Phe)+G12(Leu→Met)
G8(Leu→Trp)+G12(Leu→Trp or Met)
G8(Leu→Trp)+B13(Leu→Trp or Met)
E11(Val→Phe, Met or Leu)+G8(Leu→Trp, Met or Phe)
G8(Leu→Phe)+G12(Leu→Trp)

The above list of representative NO mutants is not intended to be all inclusive. The designations used to reference the mutations first identify the helix, then the residue number within the helix, followed by the wildtype amino acid and the substituted amino acid. For example, E11 (Val→Leu) refers to the eleventh residue of the E helix in which wildtype valine is substituted with leucine.

If desired, any of the above alpha globin mutations can be combined with any of the above beta globin mutations, or any of the above alpha globins can be combined with a known beta globin and vice versa to obtain desirable properties. In addition, other mutations may be added to adjust oxygen affinity. For example, the following combinations have the desired NO reaction kinetics:

1. αB10(Leu→Phe)+βE11(Val4Trp)+βPresbyterian (pres)
2. αE11(Val→Leu)+βE11(Val→Phe)+St. Mande
3. αB10(Leu→Phe)+αE7(His→Gln)+βG8(Leu→Trp)+St. Mande+βProvidence (prov)
4. αB10(Leu→Phe)+αE7(His→Gln)+βG8(Leu→Trp)+βprov+βpres
5. αB10(Leu→Trp)+αE7(His→4Gln)+βE11(Val→Trp)
6. αB10(Leu→Trp)+αE7(His→Gln)+αE11(Val→Leu)+αG8(Leu→Trp)+βE7(His→Gln)+βE11(Val→Met)+PG8(Leu→Trp)
7. αB10(Leu→Trp)+αE11(Val→Leu)+αG8(Leu→Trp)+βE7(His→Gln)+βE11(Val→Met)+βG8(Leu→Trp)
8. αB10(Leu→Trp)+αE11(Val→Phe)+αG8(Leu→Trp)+βE11(Val→Leu)+βG8(Leu→Trp)
9. αB10(Leu→Trp)+αE11(Val→Phe)+βE11(Val→Met)+βG8(Leu→Trp)
10. αB10(Leu→Trp)+αE11(Val→Phe)+βE7(His→Gln)+βE11(Val→Met)+βG8(Leu→Trp)
11. αB10(Leu→Trp)+αE11(Val→Phe)+αG8(Leu→Ile)+βE11(Val→Leu)+βG8(Leu→Trp)
12. αB10(Leu→Trp)+αE11(Val→Phe)+αG8(Leu→Ile)+βE11(Val→Met)+βG8(Leu→Trp)
13. αB10(Leu→Phe)+αE7(His→Gln)+βG8(Leu→Trp)
14. αB10(Leu→Phe)+αE7(His→Gln)+βE11(Val→Trp)
15. αB10(Leu→Phe)+αE7(His→Gln)+βG8(Leu→Trp)+βE11(Val→Trp)
16. αB10(Leu→Phe)+αE7(His→Gln)+βG8(Leu→Trp)
17. αB10(Leu→Trp)+αE7(His→Gln)+βE11(Val→Trp)+βprov
18. αB10(Leu→Phe)+αE7(His→Gln)+βG8(Leu→Trp)

Although the following mutations were introduced into di-alpha constructs, the described combinations can be placed into mono-alpha constructs as well:

di α Constructs (Substitutions in Both α Subunits):
1. αB10(Leu→Trp)+αE7(His→Gln)+βE7(His→Tyr)+βG8(Leu→Trp)
2. αB10(Leu4Trp)+αE7(His→Gln)+βE7(His→Phe)+βG8(Leu→Trp)
3. αB10(Leu→Trp)+αE7(His→Gln)+βE7(His→Tyr)+βE11(Val→Trp)
4. αB10(Leu→Trp)+αE7(His→Gln)+βE7(His→Phe)+βE11 (Val→Trp)
5. αB10(Leu→Trp)+αE7(His→Gln)+βE11(Val→Trp) [3011]
6. αB10(Leu→Trp)+αE7(His→Gln)+βG8(Leu→Trp) [3012]
7. αB10(Leu→Trp)+αE7(His→Gln)+βE11(Val→Met)+βG8(Leu→Trp) [3017]
8. αB10(Leu→Trp)+αE7(His→Gln)+βE7(His→Gln)+βB11(Val→Met)+βG8(Leu→Trp) [3019]
9. αB10(Leu→Trp)+βE11I(Val→Trp)
10. αB10(Leu→Phe)+αE7(His→Gln)+βG8(Leu→Trp) [2821]
11. αB10(Leu→4Phe)+αE7(His→Gln)+βE11(Val→Trp)
12. αB10(Leu→Phe)+βE11(Val→Trp) [3001]
13. αE11(Val→Phe)+βE11(Val→Phe)+βG8(Leu→Ile) [3002]
14. αE11(Val→Leu→)+βE11(Val→Phe) [3004]

di-α Constructs Containing the Following β Globin Substitutions):
B10(Leu→Phe)+B13(Leu→Trp)
B10(Leu→Phe)+B13(Leu→Met)
B10(Leu→Phe)+G12(Leu→Trp)
B10(Leu→Phe)+G12(Leu→Met)
B13(Leu→Trp)+E11(Val→Phe)
B13(Leu→Trp)+E11(Val→Trp)
B13(Leu→Met)+E11(Val→Phe)
B13(Leu→Met)+E11(Val→Trp)
E11(Val→Phe, Met or Leu)+G8(Leu→Trp, Met or Phe)
G8(Leu→Phe)+B13(Leu→Met)
G8(Leu→Phe)+B13(Leu→Trp)
G8(Leu→Phe)+G12(Leu→Met)
G8(Leu→Phe)+G12(Leu→Trp)
G8(Leu→Trp)+B13(Leu→Met)
G8(Leu→Trp)+B13(Leu→Trp)
G8(Leu→Trp)+G12(Leu→Met)
G8(Leu→Trp)+G12(Leu→Trp)
E11(Val→Phe or Trp)+G12(Leu→Met or Trp)

Combinations of these mutations can also be placed in larger sized hemoglobins having more than one tetramer such as, for example, di-hemoglobins (di-di alpha constructs).

In general, substitution of large hydrophobic residues at key positions in the distal heme pockets of alpha and beta globins can substantially reduce the rate of NO catalyzed oxidation (NO scavenging). However, there were exceptions to this general observation. For example, substitutions of Trp and Phe at Leu-B10 in alpha subunits profoundly lowered the NO scavenging rate (about 20 times slower) but Trp and Phe substitutions at Leu-B10 in beta did not measurably alter the NO scavenging rate.

Conversely, Trp and Phe substitutions at Leu-G8 significantly reduced the NO scavenging rate in beta (6 times slower for Trp) but had no detectable effect on the NO scavenging rate in alpha. In addition, while substitutions at Val-E11 gave reduced NO scavenging rates for both alpha and beta subunits the results were not strictly consistent with the size of the substituted amino acid (Table 3).

TABLE 3

| Mutant | Subunit | K'$_{NO, ox}$ (µM$^{-1}$ s$^{-1}$) |
| --- | --- | --- |
| Val-E11 (wild-type) | α | 70 |
| Trp at Val-E11 | α | 22 |
| Phe at Val-E11 | α | 26 |
| Leu at Val-E11 | α | 16 |
| Val-E11 (wild-type) | β | 60 |
| Trp at Val-E11 | β | 5 |
| Phe at Val-E11 | β | 12 |
| Leu at Val-E11 | β | 16 |

In alpha subunits the smallest amino acid (leucine) produces the greatest reduction in NO scavenging rate. In beta subunits the results are more consistent with the prediction that increasing bulk and hydrophobicity will reduce the NO scavenging rate.

Amino acid substitutions obtained from the mutant libraries were also generally consistent with the theme of large hydrophobic residues promoting reduced rates of NO scavenging. Among mutants identified in this screen as having significantly reduced rates of NO catalyzed oxidation, there was a preponderance of substitutions such as Trp, Phe, Leu, Met, Val and Ile. However, some mutant heme pockets containing unusual hydrophilic residues such as Thr, Ser, Tyr and His were also observed to have substantially reduced NO scavenging rates. While such substitutions might be expected to lead to unstable molecules due to rapid autooxidation, it is possible that some of these molecules could exhibit novel and useful properties.

The NO mutants of the present invention should have a rate constant for reaction of NO with oxyhemoglobin (k'$_{NO, ox}$) less than conventional hemoglobin, preferably in the range of about 0.1 µM$^{-1}$s$^{-1}$ to less than about 60 µM$^{-1}$s$^{-1}$. Preferabl the rate constant is less than 25 µM$^{-1}$s$^{-1}$, more preferably between 12 and 15 µM$^{-1}$s$^{-}$, and most preferably less than 5 µM$^{-1}$s$^{-1}$.

Of the NO mutants produced that were tested in vivo, the results demonstrate a linear correlation between the magnitude of the pressor effect in vivo and the in vitro rate of NO scavenging. For example, reducing the NO reactivity of the heme groups significantly reduced the magnitude of the pressor response in conscious rats.

Accordingly, the data support the hypothesis that the pressor response to extracellular hemoglobins is due to a decrease in steady-state levels of NO in the region of the endothelial and smooth muscle cells lining the vasculature. A decrease in NO concentration results in lesser activation of guanylyl cyclase, which ultimately increases the tone of vascular smooth muscle. It is believed that following administration of cell-free hemoglobin, a competition exists for the available NO between guanylyl cyclase and ferrous oxy- and deoxyhemoglobin (extravasation of the hemoglobin into or through the endothelium may be required). Those recombinant hemoglobins that have lower rates of reaction with NO are less potent competitors for nitric oxide. Consequently, the NO mutants of the present invention are useful for a variety of applications because due to their intrinsic lower reactivities, they produce little or no perturbation in the natural turnover of nitric oxide, but remain capable of binding and delivering oxygen.

The results also demonstrate that if the amino acid substitutions used to reduce NO scavenging have an undesirable effect on oxygen delivery, the P$_{50}$ and rate of O$_2$ dissociation can be "corrected" by other strategically placed amino acid substitutions. O$_2$ kinetics and equilibria can be manipulated by changing the position of the allosteric equilibrium, or by altering the intrinsic binding kinetics and affinity of the subunits. Mutations away from the distal heme pockets can be used to change the relative stabilities of the high-affinity "R" and low-affinity "T" allosteric states. Hemoglobin allostery has a significant effect on oxygen binding, but no effect on oxidation by NO.

The intrinsic O$_2$-binding properties of each subunit can be modified by varying the degree of steric hindrance near the iron atom, or by varying the strength of hydrogen bonding between the E7 residue and the bound oxygen. Steric hindrance affects the association and dissociation rate constants by altering the entry and exit of oxygen to and from the heme pocket. Similarly, steric hindrance also affects the rate of oxidation by NO. The E7 histidine stabilizes bound oxygen through hydrogen bonding interactions. Substitution of the E7 histidine can decrease the degree of stabilization of bound oxygen and enhance oxygen dissociation kinetics. E7 substitutions can also affect reactivity of NO with Hb.

Figure 11:
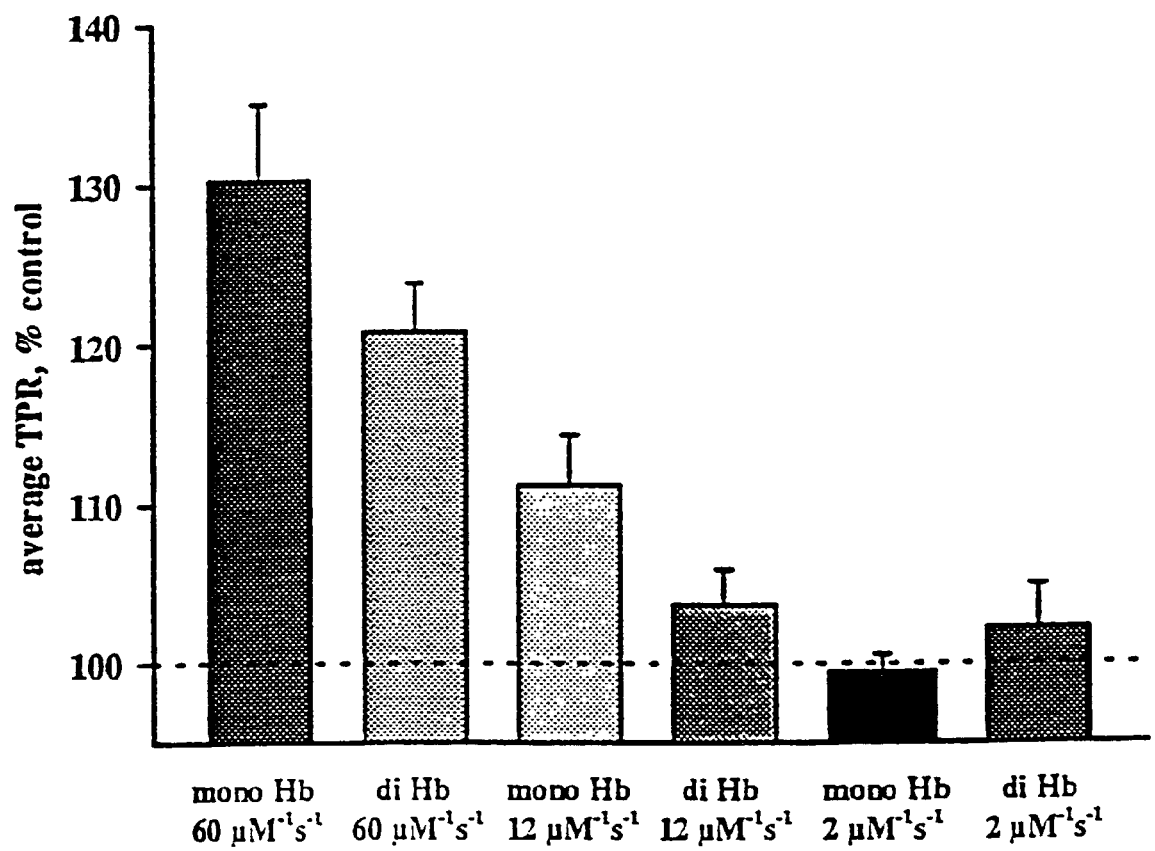
FIG. 11 shows the average total peripheral resistance (TPR) response to recombinant hemoglobins. The average TPR was calculated from data collected starting 20 minutes and ending 90 minutes following administration. The dose used in each case was 350 mg Hb/kg body weight. "Mono Hb" refers to single-tetramer Hb species (MW about 64,000), and "di Hb" indicates two Hb tetramers that are genetically fused (MW about 128,000). The rate constant for NO-oxidation of each rHb is noted on the abscissa.
Figure 12:
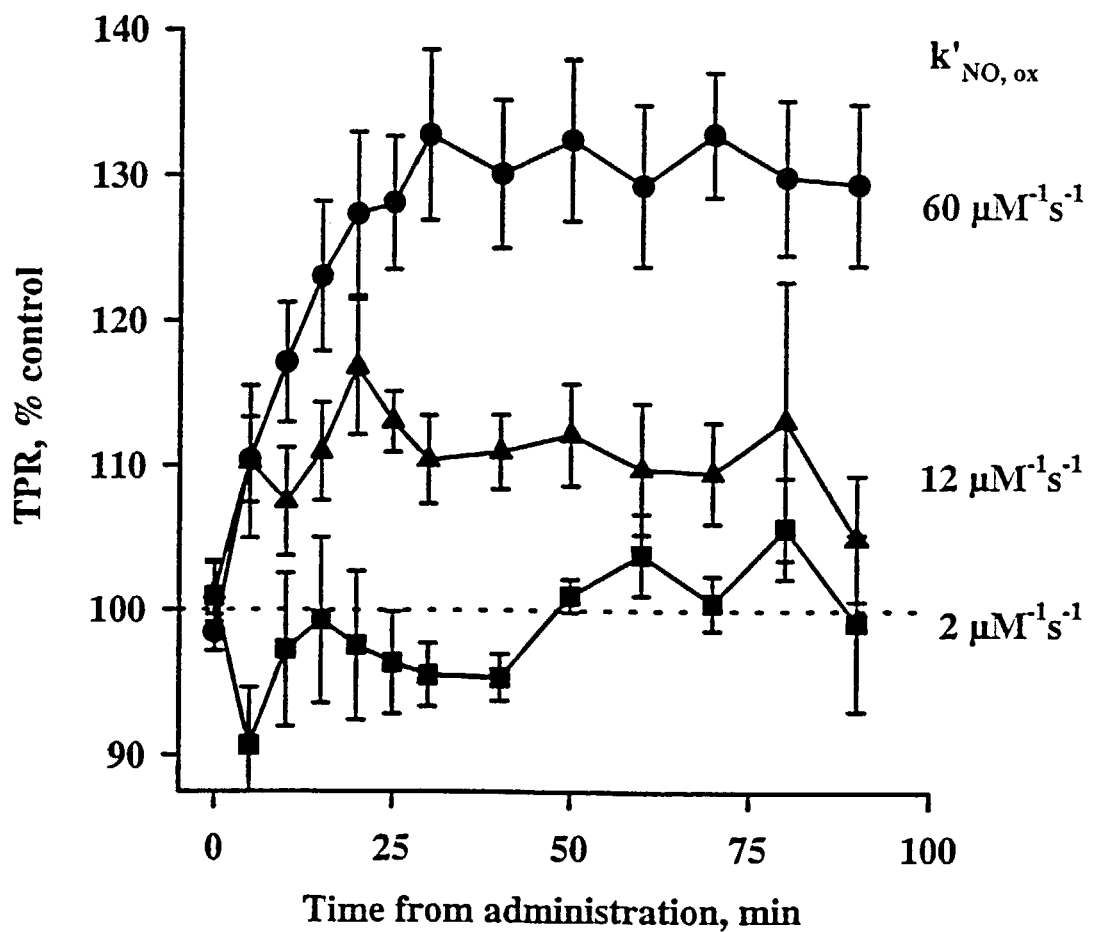
FIG. 12 shows the TPR responses to three recombinant hemoglobins. Changes in TPR are plotted as percent of pre-administration values versus time from administration. AU hemoglobins contained a genetically fused dialpha subunit to prevent dissociation into αβ dimers. The rate constant for reaction of nitric oxide with each rHb is noted beside each data set. Hemoglobin doses were always 350 mg/kg.
Figure 13:
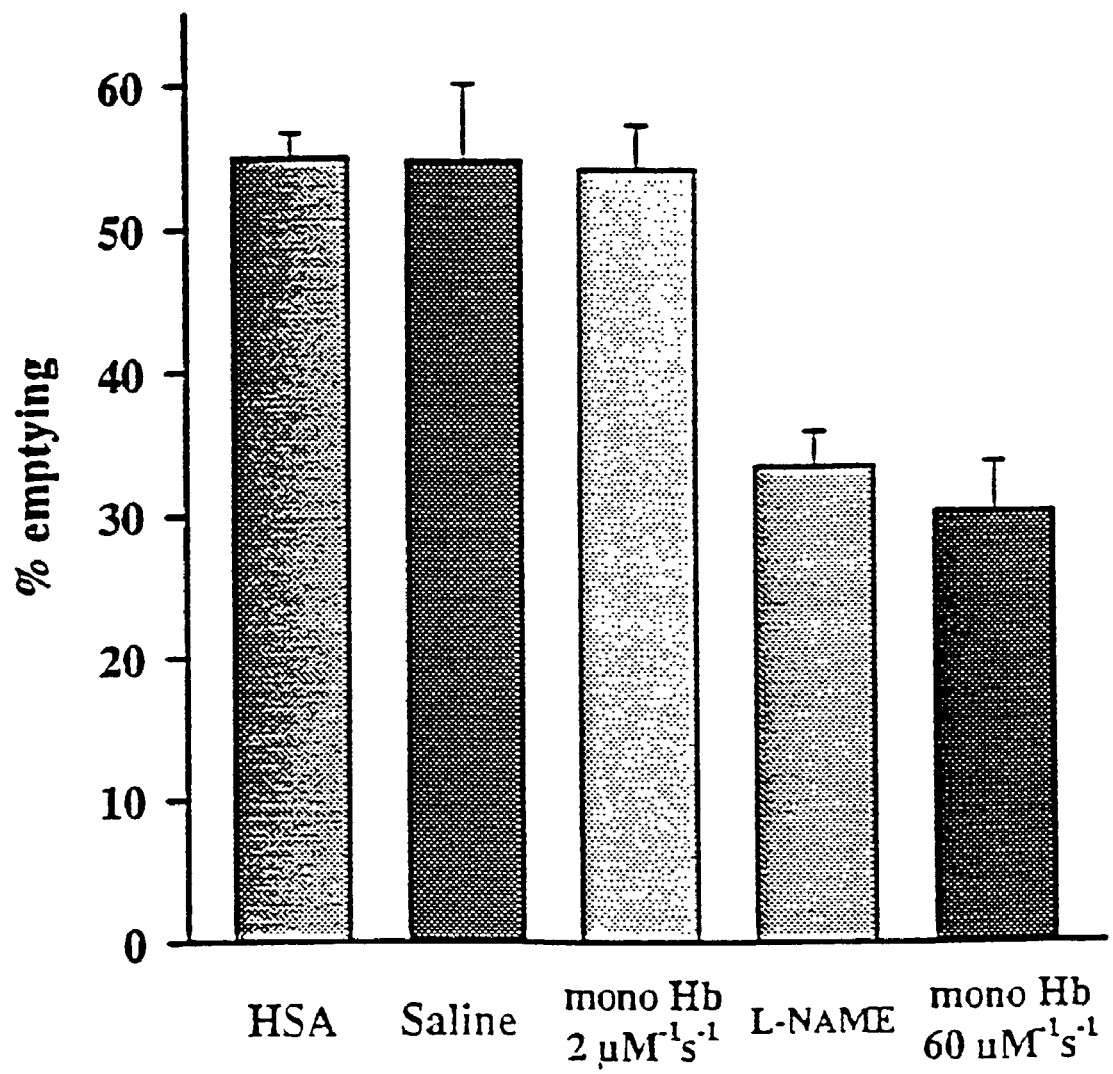
FIG. 13 shows the results of the gastric emptying model of GI motility. Greater scavenging of nitric oxide, or inhibition of synthesis of nitric oxide, decreases emptying of the stomach. The dose used for each protein was 750 mg Hb/kg body weight (10% solution) and the dose for L-NAME was 10 mg/kg.

The results further demonstrate the beneficial effects of increasing the size of the hemoglobin molecule, which is additive to the effects of amino acid substitutions used to reduce NO scavenging as shown in FIG. 11.

The recombinant hemoglobins of the present invention can be used for a number of in vitro or in vivo applications. Such in vitro applications include, for example, the delivery of oxygen by compositions of the instant invention for the enhancement of cell growth in cell culture by maintaining oxygen levels in vitro (DiSorbo and Reeves, PCT publication WO 94/22482, herein incorporated by reference). Moreover, the hemoglobins of the instant invention can be used to remove oxygen from solutions requiring the removal of oxygen (Bonaventura and Bonaventura, U.S. Pat. No. 4,343,715, incorporated herein by reference) and as reference standards for analytical assays and instrumentation (Chiang, U.S. Pat. No. 5,320,965, incorporated herein by reference) and other such in vitro applications known to those of skill in the art.

In addition, the recombinant hemoglobins can be formulated for use in various therapeutic applications. Example formulations suitable for the recombinant hemoglobin of the instant invention are described in Milne, et al., WO 95/14038 and Gerber et al., WO 96/27388, both herein incorporated by reference. Pharmaceutical compositions can be administered by, for example, subcutaneous, intravenous, or intramuscular injection, topical or oral administration, large volume parenteral solutions, aerosol, transdermal or mucus membrane adsorption and the like.

For example, the recombinant hemoglobins of the present invention can be used in compositions useful as substitutes for red blood cells in any application that red blood cells are used or for any application in which oxygen delivery is desired. The recombinant hemoglobins can also be formulated as oxygen carrying therapeutics and used for the treatment of hemorrhages, traumas and surgeries where blood volume is lost and either fluid volume or oxygen carrying capacity or both must be replaced. Moreover, because the recombinant hemoglobins of the instant invention can be made pharmaceutically acceptable, they can be used not only as blood substitutes that deliver oxygen but also as simple volume expanders that provide oncotic pressure due to the presence of the large hemoglobin protein molecule.

In a further embodiment, the recombinant hemoglobins of the instant invention can be crosslinked by methods known in the art and used in situations where it is desirable to limit the extravasation or reduce the colloid osmotic pressure of the hemoglobin-based blood substitute. Thus, the recombinant hemoglobins can act to transport oxygen as a red blood cell substitute, while reducing the adverse effects that can be associated with excessive extravasation.

A typical dose of recombinant hemoglobin as an oxygen delivery agent can be from 2 mg to 5 grams of hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a number of administrations. The selection of dosage depends upon the dosage form utilized, the condition being treated, and the particular purpose to be achieved according to the determination of those skilled in the art.

Administration of recombinant hemoglobin can occur for a period of seconds to hours depending on the purpose of the hemoglobin usage. For example, as an oxygen carrier, the usual time course of administration is as rapid as possible. Typical infusion rates for hemoglobin solutions as oxygen therapeutics can be from about 100 ml to 3000 ml/hour.

In a further embodiment, the hemoglobins of the instant invention can be used to treat anemia, both by providing additional oxygen carrying capacity in a patient that is suffering from anemia, and/or by stimulating hematopoiesis as described in PCT publication WO 95/24213, incorporated herein by reference. When used to stimulate hematopoiesis, administration rates can be slow because the dosage of hemoglobin is much smaller than dosages that can be required to treat hemorrhage. Therefore the recombinant hemoglobins of the instant invention can be used for applications requiring administration to a patient of high volumes of hemoglobin as well as in situations where only a small volume of the hemoglobin of the instant invention is administered.

Because the distribution in the vasculature of extracelluar hemoglobins is not limited by the size of the red blood cells, the hemoglobins of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, all types of tissue ischemia can be treated using the hemoglobins of the instant invention. Such tissue ischemias include, for example, stroke, emerging stroke, transient ischemic attacks, myocardial stunning and hibernation, acute or unstable angina, emerging angina, infarct, and the like. Recombinant hemoglobin can also be used as an adjunct with radiation or chemotherapy for the treatment of cancer.

Because of the broad distribution in the body, the recombinant hemoglobins of the instant invention can also be used to deliver drugs and for in vivo imaging as described in WO 93/08842, incorporated herein by reference.

Recombinant hemoglobins can also be used as replacement for blood that is removed during surgical procedures where the patient's blood is removed and saved for reinfusion at the end of surgery or during recovery (acute normovolemic hemodilution or hemoaugmentation). In addition, the recombinant hemoglobins of the instant invention can be used to increase the amount of blood that can be predonated prior to surgery, by acting to replace some of the oxygen carrying capacity that is donated.

The following Examples are intended to illustrate, but not limit, the present invention. Examples 1–16 are studies relating to increasing soluble yield of recombinant hemoglobins expressed in E.coli, while Examples 17–22 are studies relating to hemoglobin mutants having reduced NO scavenging.

EXAMPLE 1

Genetic Construction

PCR based cassette mutagenesis was used to incorporate desired amino acid substitutions. DNA sequence for variant codons was based on codons used in proteins that are highly expressed in E.coli as described in Sharp et al., Nucl. Acids Res., 16:8207–8211 (1988). In general, strains were constructed by transformation of the plasmid DNAs into E. coli strains lacking a plasmid using the procedure of Chung, et al. Proc. Natl. Acad. Sci. USA, 86:2172–2175 (1989), or Hanahan, DNA Cloning: A Practical Approach, V. 1, pp. 109–135 (IRL Press, 1985).

A variety of E.coli strains were used, including those listed in Tables 4 and 5. The construction of these strains, especially those containing different oligomerizing mutants or domains, is described in WO 97/04110, incorporated herein by reference. Tables 4 and 5 summarize the strain background and plasmid backbone used for the expression of these molecules. Plasmid copy number has been shown to influence soluble expression yields as well. The medium copy plasmid pSGE705 served as a platform for some of the molecules tested. Plasmids pSGE715 and pSGE720 are high copy number plasmids, and expression from these plasmids should exceed that observed from pSGE705-based plasmids. pSGE720 contains a synthetic operon composed of the di-α-globin and βPresbyterian-globin genes transcribed from the sac promoter on a tetracycline resistant plasmid with the pUC high copy number origin of replication (Weickert & Curry, Arch. Biochem. Biophys. 348:337–346 (1997)).

TABLE 4

| SGE | plasmid | bkgrd. strain | alpha | beta |
|-----|---------|---------------|-------|------|
| 1464 | pSGE720 | 1675 | di- | presby |
| 2784 | pSGE720 | 1675 | di- | prov |
| 2706 | pSGE720 | 1675 | di- | wt |
| 2782 | pSGE720 | 1675 | di- | presby + prov |
| 939 | pSGE705 | 1661 | di-di-1 | presby |
| 2791 | pSGE705 | 1661 | di-di-1 | wt |
| 946 | pSGE720 | 1675 | di-di-1 | presby |
| 3085 | pSGE720 | 1675 | di-di-1 | prov |
| 948 | pSGE705 | 1661 | di-di-2 | presby |
| 2951 | pSGE720 | 1675 | di-di-2 | prov |
| 953 | pSGE715 | 1661 | di-di-3 | presby |
| 2952 | pSGE720 | 1675 | di-di-3 | prov |
| 955 | pSGE715 | 1661 | di-GCN4-di | presby |
| 2792 | pSGE715 | 1675 | di-GCN4-di | wt |
| 2795 | pSGE720 | 1675 | di-GCN4-di | presby + prov |
| 2796 | pSGE720 | 1675 | di-GCN4-di | prov |
| 2802 | pSGE720 | 1675 | di-P53 | presby |
| 2948 | pSGE720 | 1675 | di-P53 | prov |
| 2944 | pSGE720 | 1675 | di-COMP | presby |
| 2813 | pSGE720 | 1675 | di-COMP | prov |
| 3083 | pSGE720 | 2761 | di-K158C | presby |
| 3172 | pSGE720 | 2761 | di-K158C | presby + prov |
| 3084 | pSGE720 | 2761 | di-K158C | prov |

TABLE 5

| Strain | Plasmid | rHb | Host Descrip. |
|---|---|---|---|
| SGE1675 | none | none | gyrA96(Nal$^R$), lacI$^{Q1}$, endA, hsdR17, relA1, supE44, recJ (a deriv. of JM107) |
| SGE1464 | pSGE720 | 1.1 | SGE1675 |
| SGE1480 | pSGE726 | 1.0 | SGE1675 |
| SGE1483 | pSGE728 | 0.0 | SGE1675 |
| SGE2706 | pSGE733 | 0.1 | SGE1675 |
| SGE2761 | none | none | SGE1675 + rpsL (strR) by P1 transduction |
| SGE2782 | pSGE767 | 9 + 1.1 | SGE1675 |
| SGE2784 | pSGE768 | 9.1 | SGE1675 |
| SGE3083 | pSGE1001 | mut. | SGE2761 with rHb di-αK158C/βK82D |
| SGE3084 | pSGE1222 | mut. | SGE2761 with rHb di-αK158C/βK82D |
| SGE3138 | pMON7124K | none | gyrA96(Nal$^R$), lacI$^{Q1}$, endA, relA1, supE44, recJ (a deriv. of SGE1675) |
| SGE3172 | pSGE1237 | mut. | SGE2761 with rHb di-αK158C/βN108K; K82D |
| SGE3261 | pSGE768 | 9.1 | SGE3138 |

EXAMPLE 2

Construction of Beta Mutations pSGE728 was constructed by XhoI digestion and deletion from pSGE720 of one alpha subunit and the di-alpha glycine linker. The resulting plasmid, pSGE726, contains a single alpha gene rather than a di-alpha gene (rHb1.0). The Presbyterian mutation in beta was replaced by digestion with BglII and HindIII, and ligation to introduce wild-type beta and create pSGE728 (rHb0.0). The Presbyterian mutation in the beta gene of pSGE720 was replaced by digestion and ligation as for pSGE728, to introduce wild-type beta and created pSGE733 (di-alpha and wild type beta; rHb0.1).

The Providence mutation (βLys82→Asp) was introduced into the rHb1.1 background to create rHb9+1.1. The Lys82→Asp mutation was created by PCR amplification of a portion of the β-globin gene using an oligonucleotide containing an Asp codon in place of the Lys82. CBG124 (wild-type beta coding sequence 5' primer near BspEI site) and CBG119 (3' primer containing the βK82D mutation downstream of Asp718 site) were used to amplify a small DNA fragment from pSGE761 as template.

```
CBG119 5'AGC GAA GGT ACC GTC CAG GTT    (SEQ.ID.NO:1)

CBG124 5'CCT GAC TCC GGA AGA AAA ATC C (SEQ.ID.NO:2)
```

The PCR product and vector were digested with BspEI and Asp718 and ligated. DNA sequencing of plasmid isolated from transformants was performed with Sequenase® kit reagents and protocols (United States Biochemical, $^{33}$P (Amershim, Inc.), and primers synthesized on an Applied Biosystems 380B DNA synthesizer. Sequencing confirmed the Providence and Presbyterian mutations and the plasmicd (pSGE767) was transformed into SGE1675 to produce SGE2782.

The Providence mutation was introduced into the rHb0.1 background to create rHb9.1. A BamHI/Asp718 fragment from pSGE767 was isolated and ligated into digested pSGE733 (rHb0.1). Sequencing confirmed the mutation and the plasmid (pSGE768) was transformed into SGE1675 to produce SGE2784, or SGE3138 to produce SGE3261. Similar steps were used to introduce Providence$_{(asp)}$ and the combination of Providence$_{(asp)}$ and Presbyterian in a plasmid with a di-alpha Lys158→Cys mutation (Table 5: SGE3083, SGE3084 and SGE3172).

EXAMPLE 3

A. Bacterial Growth and Lysis Procedures

Each isolate tested was grown overnight at 37° C. as a patch on an LB plate supplemented with tetracycline. Inoculums were transferred via sterile toothpicks to 0.75 ml aliquots of fresh DM-1 media as described in Looker et al., (1992), supra, with 15 µg/ml tetracycline, 0.1 M IPTG (Sigma) and 0.05 mg/ml hemin (Ameresco) in sterile 12 mm (i.d.) borosilicate tubes. The cultures were incubated at 30° C. for 18 hours with 350 rpm shaking in a New Brunswick Series 25 Incubator Shaker. The 0.2 ml aliquots were transferred to a 96 well flat bottom microtiter plate (Immunlon 4 from Dynatech). The optical density of each well was recorded at 650 nm using the Spectral Dynamics microplate reader and Softmax software package. The cells were pelleted to the bottom of the microplates at 3000 rpm at 4° C. for 10 minutes using the Beckman RK6 centrifuge, 3.7 rotor and microplate adapter buckets. The spent media was removed and the cells were resuspended in 0.1 ml 25 mM Borax with light vortexing of microplate. The microplates were covered with parafilm and stored at −80° C. overnight and then thawed at 30° C. in a water incubator until just thawed. Lysozyme (Ameresco Ultra pure grade) was added to 0.17 mg/ml final volume from a 1 mg/ml stock containing 0.05 M NaCl. The samples were mixed by light vortexing of microplate, covered and incubated at room temperature for 30 minutes. DNAase I (Boehinger Mannheim grade II from bovine pancreas) was added to 0.02 mg/ml from 0.1 mg/ml DNAase stock containing 7.5 mM CaCl$_2$ and 75 mM MgCl$_2$. The samples were mixed by light vortexing of microplate, covered and incubated at room temperature for 15 minutes. The microplates were covered with parafilm and stored at −80° C. for 90 min. to 20 hours and then placed at 30° C. in a water incubator until just thawed. The cell debris were pelleted to the bottom of the microplates at 3000 rpm at 4° C. for 10 minutes using the Beckman RK6 centrifuge, 3.7 rotor and microplate adapter buckets. The cleared lysate was transferred to wells of a fresh microplate and stored at 4° C. for approximately 12 hours.

B. ELISA

Cleared lysates were diluted 1:800 or 1:1600 into PBS with 0.1% (w/v) casein and 1.08% (w/v) Tween 80. Recombinant di-alpha hemoglobin (rHb) standards were diluted serially into this buffer and used in the procedure in order to produce a standard curve. For the following procedure, all reagents were added in 0.1 ml aliquots unless otherwise indicated. Aliquots of 5 µg/ml goat affinity purified anti-rHb1.1 antibodies in Borate Buffered Saline were used to coat wells of Immulon 4 microplates (Dynatech) for 18 hours at 4° C. The wells were then completely filled with casein blocker (Pierce) for a short time to block nonspecific binding. After washing the plates thrice with ELISA wash buffer, diluted samples and standards were then added and the plates were incubated at 37° C. for 60 minutes. The plates were washed as above and biotin labeled Goat anti-rHb1.1 antibody at 50 ng/ml in PBS with 1% casein were added to each well. The plates were covered and incubated at 37° C. for 60 minutes and were washed as above. A 1:10,000 dilution of Streptavidin-Horse Radish Peroxidase (Southern Biotechnology Associates) into 0.1% casein in PBS was prepared and distributed and the plates were covered and incubated at 37° C. for 20 minutes and were washed as above. Working TMB Peroxidase Substrate Solution B was prepared according to manufacturer's instructions (Kiekegaard) and quickly added. After 10 minutes, 1 M phosphoric acid was added to each well to quench the reaction. The absorbance at λ450–650 nm was read for each plate. The values were then normalized against the standard curve and adjusted for dilution and for the original culture optical density at 650 nm.

EXAMPLE 4

Fermentations

Fermentations were performed in a defined medium in 15L Biolaffite fermentors, generally as described in Looker et al. "Expression of Recombinant Human Hemoglobin in *Escherichia coli.*" *Meth. Enzymol.* 231:364–374.(1994) using DM59(60) medium under Glucose excess (BAR) conditions with induction for 16 hours at 28° C., except where noted. In order to minimize the contribution of day-to-day and fermentor-to-fermentor variability to the yield outcomes, some experiments distributed strains among the fermentors and sets of fermentations, such that each set of fermentations included side-by-side controls and strains were not assigned the same fermentor more than once, when possible. Induction of expression was achieved by addition of IPTG between 10 and 200 μM on attaining a cell density of an $O.D._{600}$ of approximately 30. Incubation was continued for 16 hours post induction, and hemin was added in five shots of 10, 13, 17, 17, and 17 ml at 0, 3, 6, 9, and 12 hours post induction respectively, delivering a total concentration of 0.37 g/L of hemin. One ml fermentation samples were withdrawn at 4, 8, 12, 14 and 16 hours post induction and assayed for soluble rHb1.1. In other studies, hemin was added in five shots at 25 ml each and collected at 12, 14 and 16 hours.

EXAMPLE 5

Determination of Percent Soluble and Insoluble rHb

The accumulation of soluble and insoluble rHb was measured from at least 2 and usually at least 3 independent fermentations per condition examined. One ml samples were withdrawn into 1.7 ml Eppendorf tubes to appropriate times past induction. These one ml samples were centrifuged in an Eppendorf centrifuge for three minutes and the supernatants were removed. Pellets were stored at 80° C. until assayed. Soluble and insoluble rHb was determined as described (Weickert et al., *Appl. Environ. Micro.*, 63:4313–4320 (1997)) except that after SDS-PAGE electrophoresis, the rHb was detected by either silver staining or western blotting (10). Gels were silver stained using the reagents and protocol of Daiichi Pure Chemicals Co., Ltd. (Tokyo, Japan).

EXAMPLE 6

Hemin Concentration Estimation

Hemin concentration in the fermentation broth was estimated as follows: samples of fermentation broth were centrifuged and an aliquot of the supernatant was added to a solution of 300 μM Human Serum Albumin (HSA, Baxter) in 50 mM tris pH 7.5 such that the concentration of hemin did not exceed 50CM. In the presence of excess HSA, hemin forms a 1:1 complex with a well defined absorbance spectrum as dexribed in Beaven et al., *Eur. J. Biochem.*, 41:539–456 (1974), and the hemin concentration was estimated from the absorbance at 625 nm. By subtracting the new hemin concentration from that of the previous sample, the quantity of hemin bound by or taken up by the cells was calculated during the entire time course of rHb accumulation.

EXAMPLE 7

Comparison of Presbyterian Beta and Wild-Type Beta

Relative to Hb containing wild-type beta, expression of hemoglobin containing Presbyterian beta only produces about half the amount of soluble hemoglobin in *E. coli*. This difference must be due to the presence of the Presbyterian mutation in beta. Recombinant hemoglobin expression improvements may therefore be achieved by improvements in the beta globin. The lower expression with beta Pres. may be due to a disruption of the molecular folding pathway by the asn108→lys change of the Presbyterian mutation, or general destabilization of the beta globin, as indicated by in vitro experiences. Table 6 shows the results of the comparison between Presyterian beta and wild-type beta.

TABLE 6

| Alpha | Beta | Expression | N |
|---|---|---|---|
| MONO | PRESBYTERIAN | 0.46 | 3 |
| MONO | WILD-TYPE | 1.0 | 3 |
| DI | PRESBYTERIAN | 0.58 | 3 |
| DI | WILD-TYPE | 1.3 | 3 |

Soluble expression normalized to expression of mono-alpha with wild-type beta globin.

EXAMPLE 8

Naturally-occurring Beta Variants

Eleven naturally occurring beta variants were selected due to their reported lower Oxygen affinity as compared to wild-type beta globin, and were cloned into the rHb expression plasmid to be co-expressed with di-alpha globin. It was believed that some of these variants possess the desired oxygen affinity without compromising soluble yield. Strains were fermented and expression was measured. The results are reported in Table 7.

TABLE 7

Relative Expression of rHb Containing Beta Globin Variants (15L Fermentations)

| Variant | Substitution | Expression* |
|---|---|---|
| Wild-type | None | 1.0 |
| Cheverly | F45S | 0.5 |
| Okaloosa | L48R | ≦0.05 |
| Korle-Bu | D73N | 0.85 |
| Vancouver | D73Y | 1.1 |
| Mobile | D73V | 0.35 |
| Tilburg | D73G | 0.40 |
| Kansas | N102T | 1.2 |
| Beth Israel | N102S | 0.67 |

TABLE 7-continued

Relative Expression of rHb Containing Beta
Globin Variants (15L Fermentations)

| Variant | Substitution | Expression* |
|---|---|---|
| Saint Mande | N102Y | 0.44 |
| Providence[asp] | K82D | 1.0 |
| Presbyterian | N108K | 0.44 |

*Soluble expression normalized to expression of di-alpha with wild-type beta globin.

Recombinant hemoglobins Kansas, Vancouver, and Providence have soluble expression equal to or greater than that of wild-type beta globin. Recombinant hemoglobins Okaloosa and Cheverly, which are reported to be slightly unstable in red blood cells (Carver & Kutlow, *International Hemoglobin Information Center Variant List. Hemoglobin* 19:37–149 (1995)) had lower expression. Isolated Presbyterian beta subunits has been observed to precipitate in vitro and are considered to be less stable compared to other beta subunits.

The effect of the Presbyterian mutation in beta suggests that alternative mutations, with less profound effects on solubility, would be useful. The Providence(Asp) mutation, βLys82→Asp, reduces the oxygen affinity of hemoglobin (Bonaventura, J., et al., 1976. J. Biol Chem. 251:7563–7571) but has no reported effect on protein stability. As a test of whether other stable naturally occurring mutations can provide equivalent functional properties to Presbyterian Beta (reduced oxygen affinity), without the expression consequences, a version of rHb1.1 that uses Providence(Asp), not Presbyterian beta was created. In accord with the previous variant nomenclature, this molecule was designated rHb9.1. An additional beta variant molecule was also created, that combined the Providence(Asp) and Presbyterian mutations. Expression of these molecules was compared to expression of rHb1.1 and rHb0.1 in 15L fermentations, and these betas were then combined with many other rHbs.

EXAMPLE 9

Effect of Beta Mutations on Di-Alpha Constructs

The expression of many different hemoglobins containing genetically fused di-alphas or with domains that might serve to oligomerize the di-alpha rHbs were examined with Providence beta globin and/or with Presbyterian beta. Hemoglobin expression levels were measured for cells obtained from 15L fermentations.

The presence of Presbyterian (N108K) beta reduced the soluble rHb yield by greater than a 2-fold for both mono and di-alpha hemoglobins (Table 6). This reduction is apparent throughout the fermentation as soluble rHb. Alternative beta subunits had a profound effect on the soluble di-alpha rHb yields (Table 4). Providence(Asp) beta (K82D), a mutation known to lower oxygen affinity, resulted in much higher soluble rHb yields than did beta containing the Presbyterian mutation (Table 8).

TABLE 8

| Strain | rHb | alpha | beta | Ave. Peak Express. | S.D. | N= |
|---|---|---|---|---|---|---|
| SGE2706 | rHb0.1 | di | wt | 1.0 | ±0.33 | 9 |
| SGE1464 | rHb1.1 | di | Presby. | 0.43 | ±0.31 | 10 |
| SGE2784 | rHb9.1 | di | Provid. | 1.07 | ±0.51 | 10 |
| SGE2782 | rHb9 + 1.1 | di | Prov + Pres | 0.84 | ±0.46 | 7 |

Peak averages are normalized to rHb0.1.

The combination of Presbyterian and Providence (Asp) mutations resulted in ~2-fold higher soluble rHb accumulation than with the Presbyterian mutation alone, indicating that Providence(Asp) at least partially "rescues" the instability associated with the Presbyterian mutation. The effect on soluble Hb accumulation is apparent throughout the fermentation as soluble rHb accumulates as shown in Table 9. Table 9 reports the data relating to the accumulation of soluble rHb during fermentations of several mutant beta globins with di-alpha. The rHb containing Providence(Asp) beta globin accumulated to the highest level. The combination of Providence(Asp) with Presbyterian in beta partially "rescued" the expression of the rHb containing Presbyterian beta, whose soluble accumulation was the lowest of all the molecules tested.

TABLE 9

| Time Post Induction (Hrs) | SGE1464 Presby. rHb1.1; N = 10 | SGE2783 Prov + Presby rHb9 + 1.1; N = 7 | SGE2706 wt beta rHb0.1; N = 9 | SGE2784 Prov. rHb9.1; N = 10 |
|---|---|---|---|---|
| 4 | 0.30 | 0.28 | 0.86 | 0.63 |
| 8 | 0.70 | 1.09 | 1.79 | 1.67 |
| 12 | 1.02 | 1.97 | 2.32 | 2.56 |
| 14 | 1.01 | 2.21 | 2.69 | 2.91 |
| 16 | 1.22 | 2.43 | 2.77 | 3.07 |

When co-expressed with di-α(rHb9.1), the Providence mutation improved the soluble expression of rHb by 47% to 25.3±5.4% of the soluble cell protein, and the total globin expression increased to 44.4±12.4% (Table 10).

TABLE 10

Effect of beta globin mutations on soluble accumulation of rHb*

| Strain | 1464 | 2782 | | 2706 | 2784 |
|---|---|---|---|---|---|
| rHb | 1.1 | 9 + 1.1 | | 0.1 | 9.1 |
| beta | Asn108→Lys | Asn108→Lys+ | Lys82→Asp | wt | Lys82→Asp |
| g/L sol | 1.0 ± 0.1 | 2.6 ± 0.5 | | 2.1 ± 0.5 | 3.1 ± 0.7 |
| ave. % sol | 8.1 ± 1.4 | 17.5 ± 14.0 | | 17.2 ± 2.2 | 25.3 ± 5.4 |
| ave. % tot. | 20.6 ± 1.6 | 35.7 ± 7.5 | | 37.8 ± 5.1 | 44.4 ± 12.4 |
| solubility[†] | 44.1 ± 4.0 | 52.4 ± 10.2 | | 50.8 ± 3.7 | 58.2 ± 5.1 |

TABLE 10-continued

Effect of beta globin mutations on soluble accumulation of rHb*

| Strain | 1464 | 2782 | 2706 | 2784 |
|---|---|---|---|---|
| N* | 3 | 5 | 3 | 3 |
| K82D incr.§ | | +116% | | +47% |

*N = number of fermentations used for determining the average % soluble and total expression.
†solubility = the % of the total globin present in soluble form. It was determined independently for each fermentation sample and the averages are shown. Note: this average is not necessarily equivalent to dividing the % Sol. rHb1.1 by the % total globin since fermentations with higher globin accumulation would have greater "weight" in an average value.
§incr. = the % increase in soluble expression with the Lys82→Asp mutation in beta globin relative to soluble expression with the identical beta globin without Lys82→Asp.

This improvement was apparent throughout the entire induction period in the fermentation (Table 11), resulting in an average soluble yield of 3.1±0.7 g/L. Soluble and total accumulation of rHb9.1 was significantly better than soluble and total accumulation of rHb0.1 under identical conditions (P<0.05; Multiple Range tests) (Table 11). Table 11 reports the data relating to soluble accumulation of four variants for up to 16 hours after induction. Heme supplementation was at 0, 3, 6, 9 and 12 hours post induction to a final concentration of 0.63 ml.

TABLE 11

| Time post induction (hrs) | Soluble rHb1.1 (% cell protein) | Soluble rHb9 + 1.1 (% cell protein) | Soluble rHb0.1 (% cell protein) | Soluble rHb9.1 (% cell protein) |
|---|---|---|---|---|
| 4 | | 6.2 | 6.1 | 6.9 |
| 8 | 5.2 | 8.4 | 10.7 | 14.6 |
| 12 | 7.5 | 12.2 | 15.9 | 18.5 |
| 14 | 7.8 | 14.9 | 17.9 | 22.4 |
| 16 | 8.1 | 17.5 | 17.2 | 25.3 |

The addition of the Providence mutation to the Presbyterian β-globin subunit (rHb9±1.1) resulted in a 116% increase in soluble accumulation (Tables 10 and 11) compared to that with the Presbyterian subunit alone (P<0.02; T-test of the means). This rescued rHb1.1 soluble expression to a level statistically indistinguishable from wild type rHb0.1 (Table 10). Molecules that accumulated to higher levels did so in part because a greater proportion of the protein accumulating within the cell remained solution (Table 12). In Table 12, total globin was measured by Western blot from samples identified in Table 11. The rHbs with higher soluble expression wer correlated with higher total globin (R-squared=0.99) and with a higher percentage of the total globin present as soluble rHb (R-squared=0.97).

TABLE 12

| Soluble Expression (% cell protein) | Total Globin (% cell protein) | Soluble Globin (% total protein) |
|---|---|---|
| 9.0 | 20.6 | 44.1 |
| 18.8 | 35.7 | 52.4 |
| 19.0 | 37.8 | 50.8 |
| 25.3 | 44.4 | 58.2 |

The presence of these beta globin mutations had similar effects on soluble accumulation of a recombinant hemoglobin having a Lys158→Cys mutation in di-alpha. The presence of Providence$_{(asp)}$ improved soluble expression from a maximum of 11.3% with the Presbyterian beta to 24.4% (FIG. 1). The combination of Providence$_{(asp)}$ and Presbyterian mutations in beta resulted in an intermediate level of expression with a maximum of 16.4% soluble globin accumulation (FIG. 1).

Table 13 shows the average peak rHb yields of various di-alpha molecules co-expressed with different beta subunits. For di-alpha and three other modified alpha molecules tested, co-expression with the Providence (Asp) subunit resulted in the highest soluble accumulation. Wild-type beta was always second best and Presbyterian beta the worst.

TABLE 13

| Oligomer Molecule | Presby | wild type | Presby + Prov | Prov |
|---|---|---|---|---|
| di-α | 1.26 | 2.91 | 2.45 | 4.39 |
| di-di-α1 | 0.30 | 1.22 | — | 3.34 |
| diα-GCN4-diα | 0.10 | 0.40 | 0.34 | 1.70 |
| diα-K158C | 1.08 | — | 2.13 | 3.36 |

Table 14 shows the effect of Providence(Asp) beta on expression of many other recombinant hemoglobin molecules. The soluble accumulation of these alpha-based oligomers was substantially improved by co-expression with Providence(Asp) beta.

TABLE 14

| Oligomer Molecule | Presby | Prov |
|---|---|---|
| di-α | 1.26 | 4.39 |
| di-di-α1 | 0.30 | 3.34 |
| di-di-α2 | 0.20 | 4.24 |
| di-di-α3 | 0.20 | 4.07 |
| diα-GCN4-diα | 0.10 | 1.70 |
| diα-P53 | 0.09 | 1.58 |
| diα-COMP | BLOD* | 1.47 |
| diα-K158C | 1.08 | 3.36 |

*BLOD = below limit of detection

Table 15 shows the soluble accumulation of additional alpha-based oligomers co-expressed with Providence(Asp) beta. The use of Providence(Asp) beta resulted in substantial accumulation of additional recombinant hemoglobin molecules, including tri- and tetra-di-alpha.

TABLE 15

| Oligomer Molecule | Relative Soluble Yield |
|---|---|
| diαGCN4 | 3.35 |
| dαi-Mnt | 3.16 |

TABLE 15-continued

| Oligomer Molecule | Relative Soluble Yield |
|---|---|
| diα-tetraZIP | 1.56 |
| triα | 1.04 |
| tetraα | 0.79 |

EXAMPLE 10

Comparison of Relative Expression in ELISA and Fermentors

Based on the promising results obtained with a few naturally occurring variants at beta D73, K83 and N102, three low-complexity libraries with all 20 amino acids at each of these three positions were created. The libraries were pre-screened by the ELISA of Example 3 and expression was subsequently verified in 15 Liter fermentations The expression results are shown in Table 16. Other variants at these 3 positions were reported by ELISA to have low expression and were not fermented. The fermentation results generally matched those predicted by ELISA in 10 out of 13 variants examined. Relative standard deviation (RSD) of expression in fermentors is generally less that 20%, while the RSD of the ELISA is about 40%.

TABLE 16

| Variant | ELISA[1] | Fermentor[2] |
|---|---|---|
| Wild-type | 1.0 | 1.0 |
| N102A | 1.3 | 0.9 |
| N102V | 0.5 | 0.7 |
| D73I | 1.3 | 1.2 |
| D73M | 1.3 | 1.1 |
| D73K | 1.3 | 0.7 |
| D73E | 1.5 | 1.2 |
| D73L | 1.4 | 0.8 |
| D73T | 1.0 | 1.0 |
| K82E | 2.1 | 1.3 |
| K82G | 1.6 | 1.3 |
| K82H | 1.6 | 0.9 |
| K82P | 2.0 | N/D |
| K82Q | 1.7 | 1.0 |
| K82S | 1.0 | 1.0 |
| K82N | 1.0 | N/D |

[1]Expression was normalized to OD600 of cultures and to the soluble level measured for rHb with di-alpha and wild-type beta. Value shown is the mean of at least 2 assays.
[2]Expression was normalized to OD600 of cultures and to the soluble level measured for rHb with di-alpha and wild-type beta. Values shown are the mean of at least two fermentations and are relative to wild-type controls run at the same time.

EXAMPLE 11

Improving Soluble rHb0.0 Accumulation by Hemin Addition

In 30° C. fermentations with 15 µM IPTG to induce rHb expression, rHb0.0 consistently accumulated to higher soluble levels than rHb 1.1 to an average of 10.0±1.1% of the soluble cell protein versus 6.5±1.6% for rHb 1.1 in 10 hours. At 28° C., with 100 µM IPTG, soluble rHb0.0 accumulated to an average of 14.1±0.4%, while rHb1.1 increased by a similar magnitude, to 9.2±2.8%. Extending the induction period from 10 to 16 hours improved the soluble accumulation of rHb1.1 to 10.9±1.9% of the soluble cell protein, but resulted in the soluble yield of rHb0.0 declining from 16.5±0.3% at 8 hours post induction to 11.0±0.3% at 14 hours post induction. Total globin remained relatively constant between 23.9±5.1% at 8 hours and 22.5±4.0% at 14 hours.

The possibility that additional heme supplementation could support continued soluble rHb0.0 accumulation was tested by including two more hemin additions, at 9 and 12 hours post induction, increasing the final concentration 85%, from 0.34 to 0.63 mM. These additions prevented the soluble rHb0.0 decline observed late in the previous fermentations. Soluble rHb0.0 accumulated to an average of 19.2±2.1% of the soluble cell protein and total globin accumulated to 28.4±8.5% of the soluble cell protein. This 75% increase in soluble hemoglobin accumulation at 16 hours post induction was highly significant (P=0.0005; T-test of the means).

EXAMPLE 12

Expression Comparisons of Four rHbs Using Higher Hemin Supplementation

Using higher hemin concentrations (0.63 mM) established for rHb0.0 in 15L fermentations at 28° C., the soluble expression of four different recombinant hemoglobins was examined in parallel fermentations (Table 17). All four strains were isogenic with identical high copy plasmids except for two globin gene differences: (1) the covalent linkage to form di-α and/or (2) the presence of the β-Presbyterian (Asn108→Lys) mutation.

A significant increase in soluble expression was observed for the two strains expressing a wild type β-globin subunit rather than β-Presbyterian (P<0.05; Multiple Range tests). The average increase in soluble rHb was about 2-fold from about 10% of the soluble cell protein to about 20% or greater (Table 17). A slight increase (about 7–17%) in soluble accumulation was correlated with the expression of the di-α subunit with both wild type and β-Presbyterian subunits.

TABLE 17

| | Effect of di-alpha and beta subunits on accumulation of soluble rHb[§] | | | |
|---|---|---|---|---|
| Strain | 1480 | 1464 | 1483 | 2706 |
| rHb | 1.0 | 1.1 | 0.0 | 0.1 |
| alpha | mono | di | mono | di |
| beta | Asn108→Lys | Asn108→Lys | wt | wt |
| g/L sol | 1.1 ± 0.2 | 1.4 ± 0.4 | 2.4 ± 0.6 | 3.1 ± 0.5 |
| ave. % sol | 9.6 ± 0.5 | 11.2 ± 4.5 | 19.8 ± 1.4 | 21.2 ± 3.4 |
| ave. % tot | 21.8 ± 1.5 | 21.8 ± 0.7 | 32.4 ± 8.5 | 54.0 ± 15.0 |
| N* | 3 | 3 | 3 | 3 |
| di-α incr. † | | +17% | | +7% |
| wt β incr. ‡ | | | +106% | +89 |

[§]Fermentations at 28° C., induced for 16 hours with 100 µM IPTG and supplemented with 5 aliquots of hemin to a final concentration of 0.63 mM. Soluble yields are from samples 16 hours post induction.
*N = number of fermentations used for determining the average % soluble and total expression.
†di-α incr. = the % increase in soluble expression with the di-alpha linker relative to the soluble expression with the unlinked alpha globin.
‡wt β incr. = the % increase in soluble expression with the wild type beta globin relative to the soluble expression with the Asn108→Lys beta globin.

EXAMPLE 13

Improving Soluble rHb9.1 Accumulation By Hemin Addition

Figure 2:
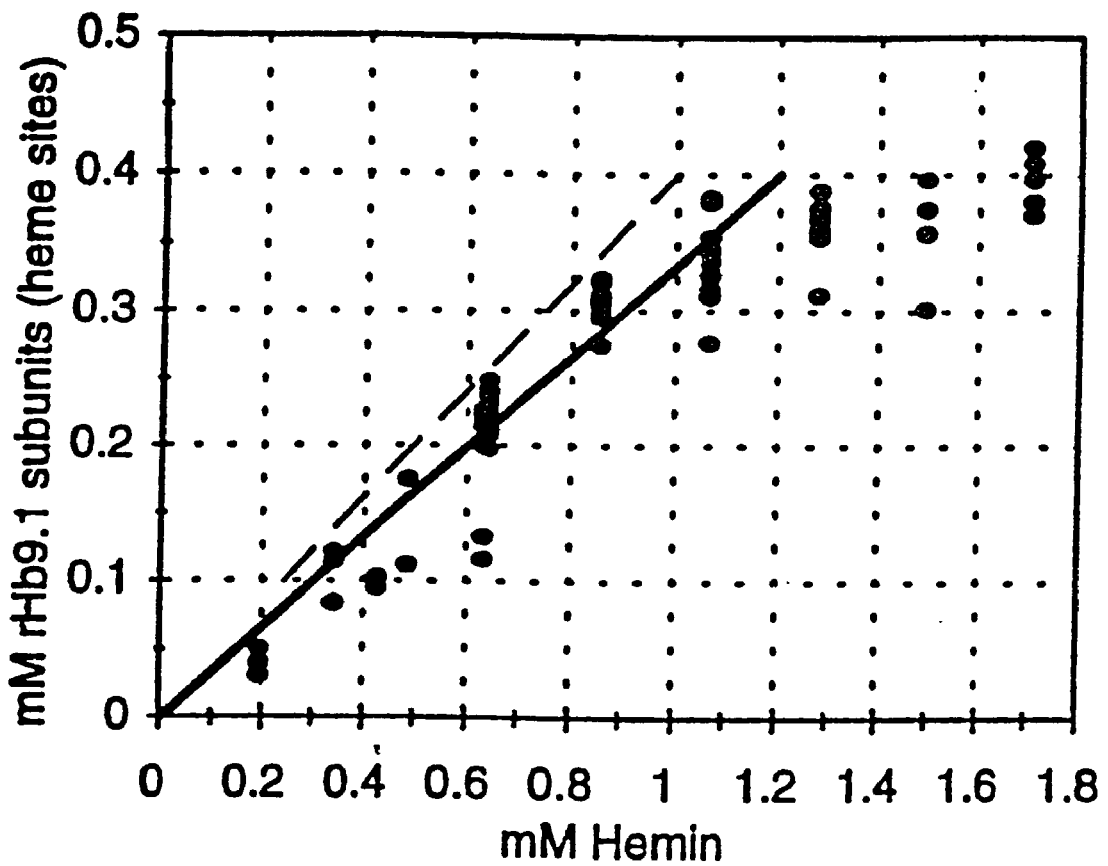
FIG. 2 shows the accumulation of soluble rHb9.1 (expressed as total hem concentration) as a function of the hemin suplied to the fermentations. Filled circles represent each of 70 individual samples. One heme site is present in each alpha and beta subunit resulting in four per hemoglobin molecule. The heavy line represents a 3-fold molar excess of hemin to heme binding sites in hemoglobin. The dashed line represents a 2.5-fold molar excess of hemin.

A 69% increase in the hemin supplementation, to 1.07 mM, significantly increased the rate of soluble rHb9.1 accumulation (FIG. 2A; P=0.001) and an average of 35.6±2.5% of the soluble cell protein, was soluble rHb9.1. These fermentations achieved an average soluble yield of 6.0±0.3 g/L rHb9.1, almost twice the 3.1±0.3 g/L achieved with the lower heme concentration (Table 18). Total rHb9.1 globin accumulation averaged 55.6±6.9% of the soluble cell protein, and total globin yield from 16 hour fermentations was 9.4 g/L. A maximum soluble accumulation of rHb9.1 to 39% of the soluble cell protein and a maximum total globin accumulation to 65% were observed from an individual fermentation. Silver stained gels of the soluble and insoluble fractions of cell lysates from fermentations reveal prominent di-α and βProvidence bands constituting the majority of the protein in each of these lysate fractions.

TABLE 18

| Time Post Induction (hours) | Soluble rHb9.1 (g/L) |
| --- | --- |
| 8 | 3.45 |
| 12 | 4.79 |
| 14 | 4.95 |
| 16 | 5.77 |
| 18 | 5.95 |
| 20 | 5.77 |
| 22 | 6.28 |
| 24 | 6.42 |

Extending the induction period to 24 hours, and continuing the hemin additions every three hours, resulted in a marginal increase in the average soluble rHb9.1 yield, from 6.0±0.3 to 6.4±0.2 g/L, but did not result in any increase in the % soluble or total rHb9.1 (Table 18). However, it resulted in the highest yield, 6.8 g/L, of soluble rHb9.1 from an individual fermentation. The effect on soluble rHb9.1 accumulation of adding at induction, a single bolus of hemin equal to the sum of hemin additions used in a typical fermentation was tested. There was no significant difference in the soluble rHb9.1 accumulation with this strategy.

EXAMPLE 14

Heme to rHb9.1 Stoichiometry

The molar concentration of hemin added was compared to the molar accumulation of soluble rHb9.1 on a per heme basis. The molar concentration of soluble rHb9.1 was calculated from the soluble yields. The molar concentration of hemin supplied was calculated from the known mass of hemin added. Each mole of hemoglobin contains 4 moles of globin subunits (2α+2βper rHb) which each contain one heme group, therefore each mole of hemoglobin contains 4 moles of heme. The accumulation of soluble rHb9.1 was strongly correlated with the amount of hemin supplied with an apparently linear relationship up to about 1 mM hemin (FIG. 3A). Addition of hemin to a concentration>1 mM did not improve soluble rHb9.1 accumulation, indicating that it was not limiting under these conditions (FIG. 3A). The correlation of accumulation of soluble rHb9.1 subunits (mM), with the mM hemin supplied was very strong over this initial concentration range (FIG. 3A; R-squared=0.90; 50 samples). The comparison indicated that an approximately three-fold molar excess of hemin was required for soluble accumulation of rHb9.1 to a range of concentrations (heavy line in FIG. 2). There was not a single sample in 70 examined that was accompanied by less than a 2.5-fold molar excess of hemin. This was therefore taken as the lower limit of hemin excess required for maximal soluble rHb accumulation.

To determine the relative importance of time of accumulation and hemin concentration, two sets of data were compared from different hemin supplementation strategies which resulted in nearly identical concentrations of hemin at different times during accumulation. One resulted in the addition of a total of 0.64 mM hemin by 6 hours post induction, and the second resulted in the addition of 0.63 mM hemin by 12 hours post induction. The concentration of soluble rHb9.1 was compared on a per heme basis at 8 hours post induction for the first condition, and 14 and 16 hours post induction for the second condition. Regardless of the time since induction, the soluble rHb9.1 accumulation was indistinguishable (0.22±0.02 mM and 0.19±0.04 mM respectively), suggesting that under these conditions, hemin was more important than time of accumulation in achieving high soluble yields.

Figure 3:
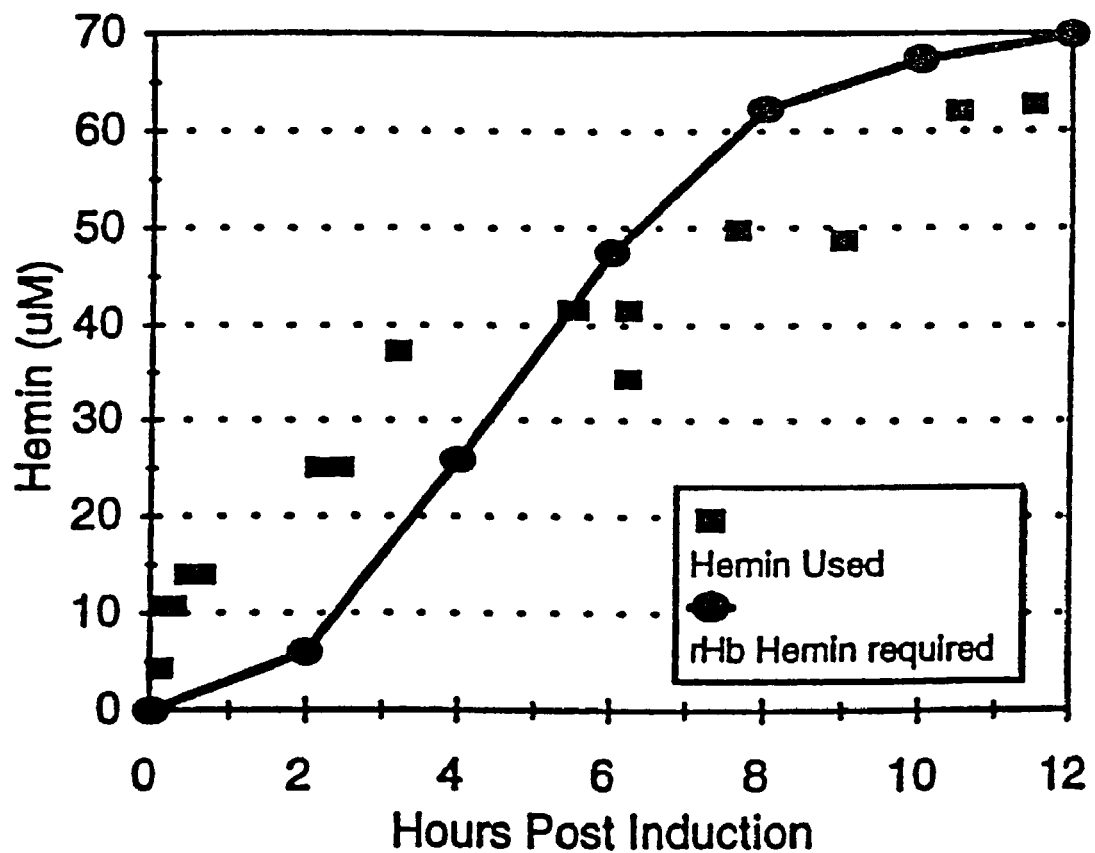
FIG. 3 shows hemin uptake and hemoglobin production. The filled squares show independent measurements of hemin loss from the fermentation broth in μMoles of hemin required for each level of rHb accumulation, assuming 4 heme molecules per rHb molecule.

The loss of heme from the media was examined in 15L fermentations, grown at 28° C., in which rHb1.1 expression was induced by the addition of 100 μM IPTG, and correlated with the accumulation of soluble rHb. An approximately stoichiometric relationship was observed, indicating that only the heme required to support soluble rHb accumulation disappeared from the media (FIG. 3).

EXAMPLE 15

Soluble Accumulation of rHb0.1 in Heme-Free Fermentations

A study was conducted to test whether rHb0.1 would accumulate to higher soluble levels than rHb1.1 in fermentations without hemin supplementation. Two fermentations at 28° C. induced with 100 μM IPTG resulted in an average soluble rHb0.1 yield of just 2.5±0.2% of the soluble cell protein, similar to that seen with rHb1.1 in Verderber et al., *J. Bacteriol.*, 179:4583–4590 (1997). Using 10 μM IPTG for induction, an average of 1.6±0.3% of the soluble cell protein was soluble rHb0.1. Dividing the soluble rHb0.1 accumulation in the absence of hernin by the accumulation in the presence of hernia an estimate was made that a maximum of 12–15% of the accumulation in the presence of hernin can be due to *E. coli* heme biosynthesis.

EXAMPLE 16

Functionality of rHbs

Samples of six variants of recombinant hemoglobins were purified. Two parameters of functionality, oxygen binding affinity ($P_{50}$) and cooperativity ($n_{Max}$) were measured (Table 19). As expected, the hemoglobin mutations affected the oxygen binding in the recombinant molecules to approximately the same degree they did in the native hemoglobin molecules. The correlation between the two functional parameters, and between each and the soluble expression levels, were examined. The two functional parameters were not correlated with each other ($R^2$=0.04; P=0.69). In spite of this, both were equally correlated with the percent soluble expression $R^2$=0.046 for P50 (P=0.14), and $R^2$=0.47 for $n_{Max}$ (P=0.13). Since the P values were greater than 0.1, the correlation of low $P_{50}$ and/or $n_{Max}$ with higher expression was not statistically significant. In addition, a sample of soluble rHb9.1 from a fermentation yielding 3.7 g/L, was examined for norvaline substitution, which had been previously observed in rHb1.1 (19, 20). The level of norvaline was below the limit of quantitation, indicating that high level soluble expression did not necessarily increase the level of this amino acid misincorporation.

TABLE 19

Effect of beta globin mutations on rHb functionality

| alpha | rHb | beta mutation | P50 | nmax |
|---|---|---|---|---|
| di- | 0.1 | wt | 10 | 2.2 |
| | 9.1 | Lys82→Asp | 15 | 2.0 |
| | 1.1 | Asn108→Lys | 31 | 2.4 |
| | 9 + 1.1 | Asn108→Lys+ Lys82→Asp | 44 | 2.2 |
| mono | 0.0 | wt | 15 | 2.6 |
| | 1.0 | Asn108→Lys | 36 | 2.6 |

EXAMPLE 17

Genetic Construction of NO Mutants

Mutations were introduced into cloned human alpha and beta genes via site directed PCR-based mutagenesis as described in general by Innis et al., *PCR Protocols: A Guide to Methods and Applications* (1990), incorporated herein by reference. In general, the desired mutations were introduced into synthetic DNA oligonucleotides which were synthesized according to the manufacturer's instructions on an Applied Biosystems 392 DNA synthesizer. Following standard deblocking procedure, oligonucleotides were dried by vacuum-centrifugation, resuspended in the desired buffer and diluted to 10–50 pmol/µl in sterile water.

Figure 4:
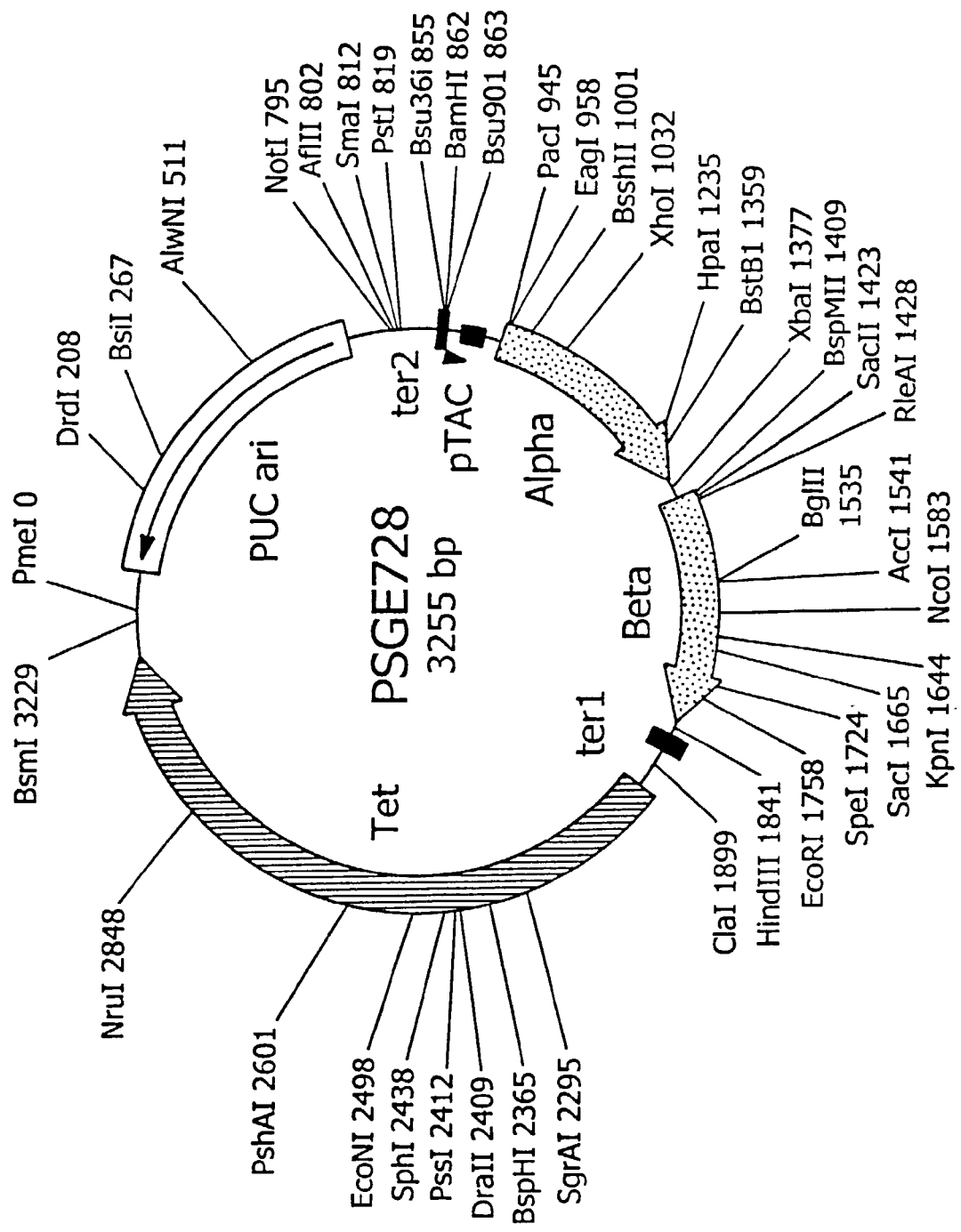
FIG. 4 shows the plasmid pSGE728 which was used for certain mutagenesis and expression experiments.

These oligonucleotides were used as primers in PCR reactions where a recombinant plasmid carrying cloned wild type alpha and beta genes, such as pSGE728 (FIG. 4), was used as template DNA.

Figure 5:
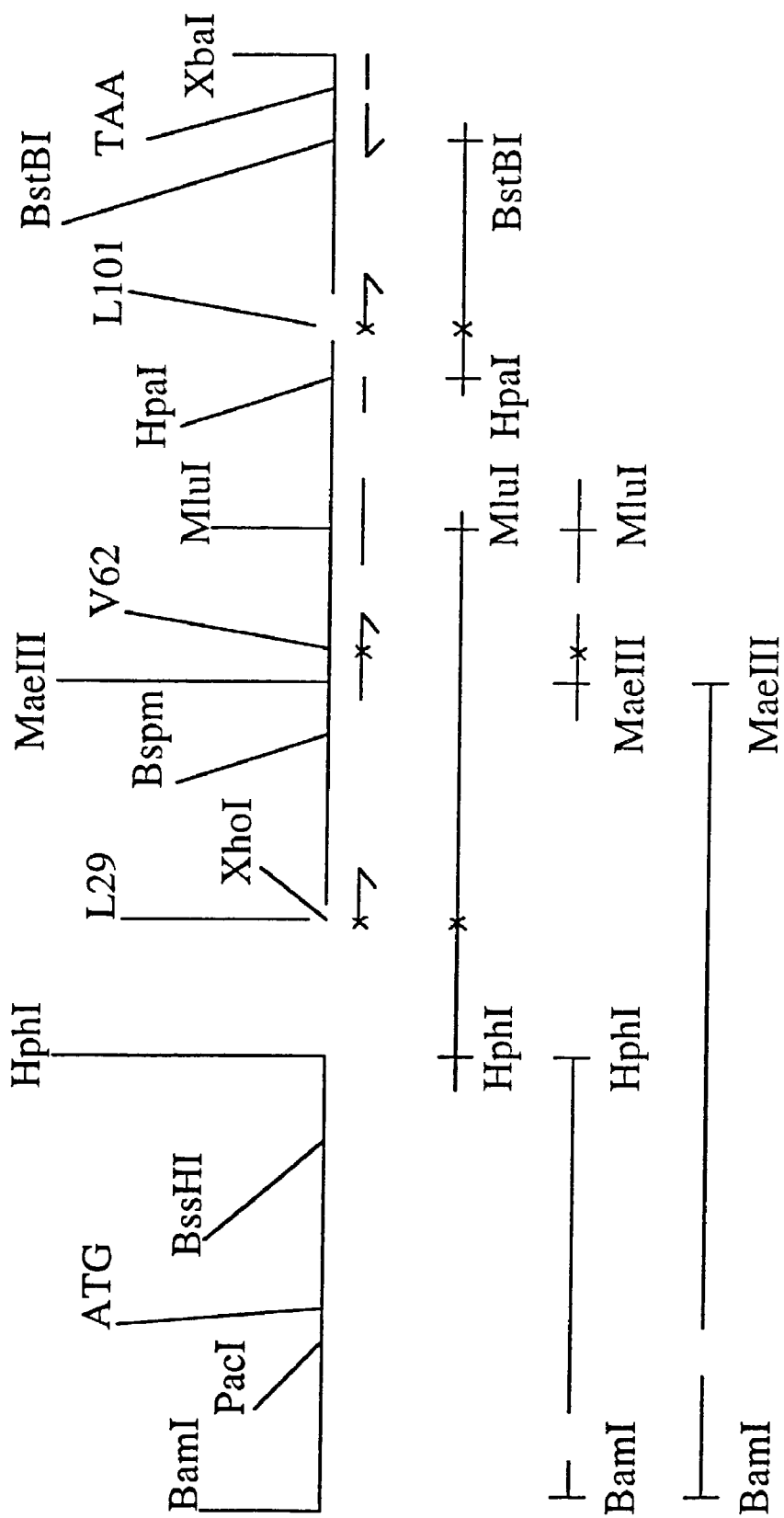
FIG. 5 shows the partial restriction map of the alpha gene inserted into pSGE728.
Figure 6:
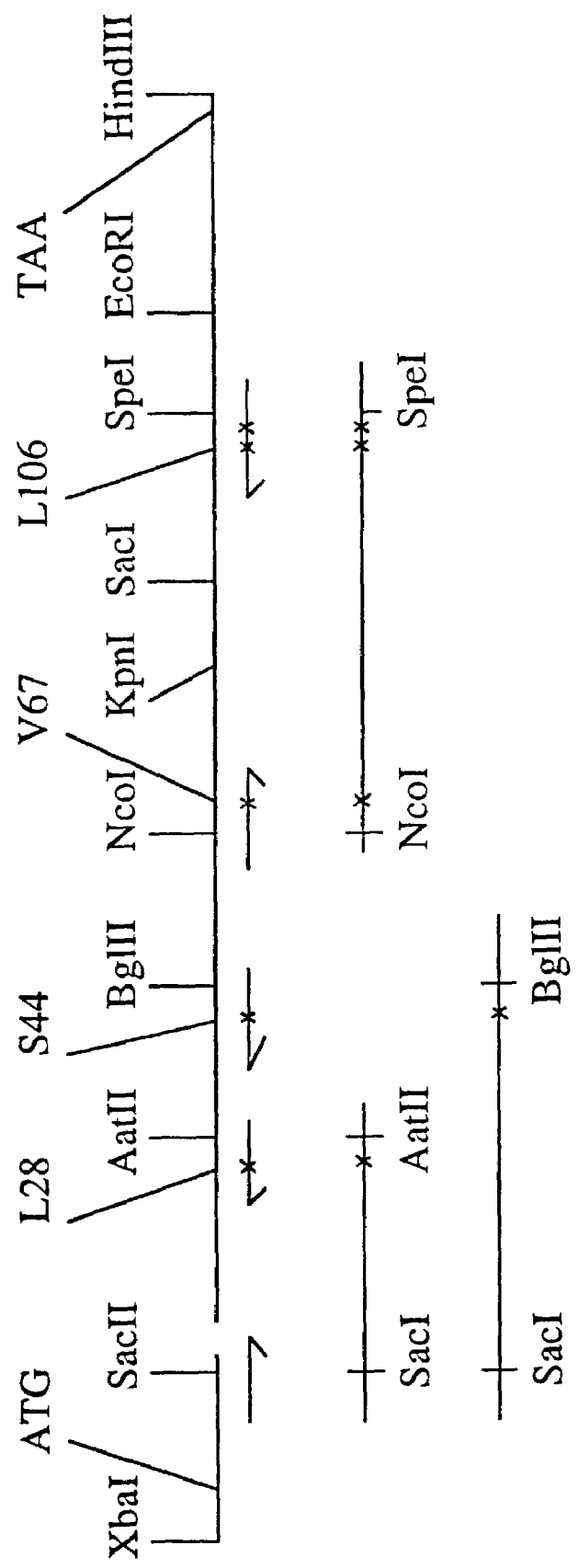
FIG. 6 shows the partial restriction map of the beta gene inserted into pSGE728.

These mutagenic oligonucleotide primers were chosen to span the site at which the mutation(s) was to be introduced and a nearby restriction endonuclease recognition site to facilitate cloning of resulting PCR products carrying mutations of interest. A second oligonucleotide primer was also required in the PCR reaction to allow DNA amplification. This primer also could be designed to contain globin gene mutation(s) or alternatively could consist of wild-type globin gene sequence from a neighboring region of the alpha or beta globin gene. This second primer was also chosen to contain a restriction endonuclease recognition site so that the resulting PCR product could be cloned into appropriately digested pSGE728 for subsequent expression of the mutated alpha or beta globin. Partial restriction maps of the alpha and beta genes from pSGE728 are shown in FIGS. 5 and 6.

The lengths of the mutagenic oligonucleotides were determined by the distance between the site to be mutated and the closest restriction site that could be incorporated into the mutagenic oligonucleotide at a position between the 5-prime end of the oligo and the site to be mutated. The mutagenic oligos were typically 30 to 45 nucleotides in length and contained mutations affecting one or two codons although more positions potentially could also be altered if desired. It was generally desirable to place the mutated DNA sequences as far as feasible from the 3-prime end of the oligo so as to avoid or minimize potential problems during the primer annealing step of the PCR reaction. The mutated nucleotides were generally placed 5–10 nucleotides upstream of the 3-prime end of the mutagenic primer. The globin gene restriction site incorporated near the 5-prime end of the mutagenic oligonucleotide was generally placed 5–12 nucleotides downstream of the 5-prime end to facilitate subsequent digestion of PCR products. Oligonucleotides which were employed solely as primers in PCR (i. e. did not contain mutations) were typically 24–36 nucleotides in length and contained globin gene restriction sites generally located 6–12 nucleotides downstream of the 5-prime end of the oligonucleotide.

PCR reactions were generally performed in an Applied Biosystems GeneAmp 9600. PCR reaction conditions were empirically determined: denaturation was typically at 95° C. for 15–60 seconds, generally annealing temperatures ranged from 45–60° C. for 15–30 seconds with many reactions being run in 50–55° C. range for annealing, and extensions were done at 720 C. for 15–120 seconds.

In some instances the annealing temperature was raised during the course of the reaction: e.g. a reaction might consist of 5 rounds with an annealing temperature of 45° C. followed by 20 rounds at an annealing temperature of 60° C. Typically reactions consisted of a total of 25–30 cycles. The reactions were typically performed in 10 mM Tris-HCl (pH 8.3), 50 mM KCl, 1.5 MM $MgCl_2$ 0.2 mM dNTPs (Pharmacia) and 0.001% gelatin. Oligonucleotide primers were added at concentrations usually 0.5–1.0 µM. Purified plasmid DNA (about 0.1–10 ng per reaction) such as pSGE728 was generally used as template. AmpliTaq® DNA Polymerase (Perkin Elmer) was typically used at 1–10 units per reaction and reaction volumes ranged from 20–100 ul.

Following the PCR reaction the reaction products were purified using the QIAquick PCR Purification Kit (QIAGEN Inc. Santa Clarita, Calif.). The purified products were then subjected to restriction endonuclease digestion with the appropriate enzymes to generate DNA fragments suitable for cloning into similarly cut pSGE728. Restriction digests were performed according to vendor protocols.

The digested PCR fragments could be cloned directly or first subjected to agarose gel electrophoresis and purified out of the agarose gels. Gel composition and electrophoresis conditions were chosen based on the DNA fragment size. Many fragments were about 60–250 base pairs in length and for these fragments resolution in gel electrophoresis is optimal with gels such as 3% NuSeive agarose or 4% Metaphor agarose, both obtained from FMC BioProducts (Rockland, Me.) and used according to vendor protocols. Following electrophoresis, DNA fragments were purified out of agarose gel slices using the QIAEX II Gel Extraction Kit (QIAGEN Inc. Santa Clarita, Calif.) according to the vendor protocols. The vector pSGE728 was also digested with the enzymes appropriate for cloning the mutagenized PCR fragment(s) of interest and similarly gel-purified following more conventional electrophoresis.

Digested and purified mutagenized PCR fragments were ligated with digested and purified pSGE728 vector fragment using T4 DNA ligase (New England BioLabs Beverly, Mass.) according to the vendor protocols and ligation products were used to transform *E coli*. *E coli* strain JM109 obtained as competent cells from Promega (Madison, Wis.) was often used for this purpose although other strains of *E coli* could also be employed as well as other various methods for preparation of competent cells (Sambrook et al., *Molecular Cloning: A Laboratory Manual* (Cold Springs Harbor, 1989)). Transformants were selected for tetracycline-resistance and could subsequently be sequenced to identify the mutations of interest and confirm the sequence of the mutagenized cloned PCR segment. Plasmid templates were prepared using the QIAprep Spin Miniprep Kit (QIAGEN) and sequenced using the AmpliCycle™ Sequencing Kit (Perkin Elmer, Foster City, Calif.) according to the vendor protocol. Some sequencing was performed manually using Sequenase (United States Biochemical, Cleveland, Ohio) but the preferred method is automated sequencing using the AmpliCycle™ Sequencing Kit (Perkin Elmer, Foster City, Calif.) to perform sequence reactions according to the vendor protocol and analysis on an ABI Prism 377 DNA Sequencer (Applied Biosystems Division of Perkin Elmer, Foster City, Calif.).

Variations of this procedure were sometimes used if a site to be mutated was not located sufficiently close to a restriction site that was unique in pSGE728. In that case a so-called "helper" DNA fragment might be employed to facilitate cloning steps. For example in the alpha gene (FIG. 5) the codon for the V62 position of that protein is somewhat distant from unique restriction sites so that the Mae III site shown in that figure, which is not unique to the plasmid but is unique to the segment from the Bam HI site to the V62 codon. Therefore, the V62 codon was mutated on a PCR fragment spanning the Mae III through Mlu I segment of the alpha gene and this fragment following Mae III digestion was ligated to a gel-purified Bam HI-MaeIII fragment of pSGE728. This ligation product was digested with Bam HI and MluI (both of which are unique cutters within pSGE728) and the Bam HI-Mlu I fragment was gel purified and ligated to Bam HI- Mlu I- and gel-purified vector fragment of pSGE728. Alternatively V62 mutations could have been incorporated into longer oligonucleotides that spanned unique sites such as Mlu I.

For construction of large libraries of mutant hemoglobins in which two to four amino acids were simultaneously mutated essentially randomly, similar procedures were followed for mutagenic oligonucleotide design, PCR reactions, and cloning steps. However, it was sometimes desirable to omit restriction sites from certain mutagenic oligos and instead to incorporate the restriction sites necessary for cloning into pSGE728 via a subsequent PCR amplification with a primer that partially overlapped this particular mutagenic oligo and spanned a useful restriction site. These amplifications needed to be performed under conditions designed to rigorously exclude environmental contaminants of wild type globin sequences such as pSGE728 and other recombinant plasmids carrying globin sequences. These sorts of environmental contaminants could potentially be preferentially primed in this latter type of amplification because they can anneal to the full length of these oligo primers whereas the PCR fragments which are the target templates only anneal to a smaller portion of such primers.

In some instances two or more mutagenized PCR segments were ligated together to create segments containing as many as four mutagenized sites prior to cloning into appropriately digested pSGE728 vector. The appropriately sized ligation products were identified and subsequently purified by agarose gel electrophoresis. In some instances the purification step was preceded or followed by PCR amplification using primers that would specifically amplify the ligation product of interest.

To generate a wide spectrum of amino acid substitutions at positions of interest, mutagenic oligos were synthesized with degeneracies at positions of interest. For "randomization" of a given position two degenerate oligos were synthesized, one of which contained the sequence N(T/A/C)T at the codon to be randomized while the other contained the sequence (A/T)(T/G)(T/G) at the same position. These two oligos could be pooled prior to PCR but more usually two independent PCR reactions were used with such pairs and the PCR products roughly quantitated (using an AlphaImager™2000 Documentation & Analysis System from Alpha Innotech Corp San Leandro, Calif.) by visualization following gel electrophoresis. Once quantitated, roughly equivalent quantities of each fragment could be pooled for subsequent cloning steps. This "randomization" results in 20 different codons generating 16 different amino acid substitutions: there are two codons each for F, I, L, and S; 1 codon for each of D, R, N, A, T, P, C, V, M, H, W, and Y. The amino acids E, K, Q, and G are absent from "randomized" positions in these libraries.

Following ligation into pSGE728 vector and transformation into $E$ $coli$, a number (typically, 24–28) of independent Transformants were picked and the mutagenized PCR segment cloned in each was sequenced. Plasmid templates were prepared using the QIAprep Spin Miniprep Kit (QIAGEN) and sequenced using the AmpliCycle™ Sequencing Kit (Perkin Elmer, Foster City, Calif.) according to the vendor protocol. Sequences were run and analyzed on an ABI Prism 377 DNA Sequencer (Applied Biosystems Division of Perkin Elmer, Foster City, Calif.). Sequences were analyzed to assess the distribution of amino acid substitutions within a given library and the frequencies of PCR-induced and synthetic oligo-induced errors in DNA sequence. Subsequently clones from libraries were picked and analyzed as described below.

EXAMPLE 18

Construction of $\alpha$ and $\beta$ Mutants (Di-alpha and Di-di-alpha)

For some studies it was desirable to produce recombinant hemoglobins that were mutated in both the alpha and beta subunits. Toward that end, alpha and beta mutations can be combined in derivatives of pSGE728. Typically such combinations can be achieved by cutting mutant derivatives of pSGE728 with appropriate restriction endonucleases that separate the alpha and beta sequences, gel-purifying the restriction fragment containing the beta gene of the mutant beta derivative of pSGE728, gel-purifying the restriction fragment containing the alpha gene of the mutant alpha derivative, ligating these two fragments together, transforming $E$ $coli$ and analyzing the resulting transformnants to verify the presence of both alpha and beta mutations.

For alpha and beta mutations at residues B10, E11, G8 and E7 such combinations can be made by digesting the mutant derivatives of pSGE728 with Bsp HI which cuts within the tetracycline-resistance gene and SacII which cuts within the beta gene, about 28 base pairs from the start of the beta coding sequence. Digestion with Sacil and BspHI (New England BioLabs, Beverly Mass.) according to the vendor protocols results in two DNA fragments: one 937 bp in length containing a portion of the gene for tetracycline-resistance and nearly all of the beta gene and including the codons for amino acid residues B10, E11, G8 and E7, and the second 2318 bp in length which contains a portion of the gene for tetracycline-resistance and all of the alpha gene. These digestion products can be readily separated by electrophoresis on agarose gels of (0.6–1.0)% using SeaKem® GTG® agarose (FMC BioProducts, Rockland, Me.) according to the vendor protocols. Subsequently the 937 bp fragment derived from the beta mutant derivative of pSGE728 can be excised out of the agarose gel and purified using the QIAEX II Gel Extraction Kit (QIAGEN Inc. Santa Clarita, Calif.) according to the vendor protocols.

Similarly the 2318 bp fragment from the pSGE728 derivative carrying the alpha mutation can also be excised from the gel and purified. These two purified fragments can be ligated together using T4 DNA ligase (New England BioLabs Beverly, Mass.) according to the vendor protocols and ligation products were used to transform *E coli*. *E coli* strain JM109 obtained as competent cells from Promega (Madison, Wis.) can be used for this purpose although other strains of *E coli* could also be employed as well as other various methods for preparation of competent cells (Sambrook et al., supra). Selection for tetracycline resistant transformants selects for reconstitution of the tetracycline-resistance gene and this is nearly always associated with reconstitution of the beta gene at the SacII site. When individual transformants thus obtained are analyzed by determining DNA sequence for alpha and beta genes and gross plasmid structure, more than 90% are found to be the desired recombinants which have both the alpha and beta mutations. For sequence analysis plasmid templates can be prepared using the QIAprep Spin Miniprep Kit (QIAGEN) and sequenced using the AmpliCycle™ Sequencing Kit (Perkin Elmer, Foster City, Calif.) according to the vendor protocol. Sequences were run and analyzed on an ABI Prism 377 DNA Sequencer (Applied Biosystems Division of Perkin Elmer, foster City, Calif.).

For some studies it is desirable to produce recombinant hemoglobins carrying amino acid substitutions in both alpha and beta and in which the alpha subunits are genetically fused by a glycine (or some other amino acid) linker. Methods have been described in Looker et al., *Nature* 356:258–260 (1992) for the construction of such "di-alpha" fusions and these methods could be applied to construct di-alpha versions of any mutant alpha gene. Such di-alpha mutants could readily be combined with any beta mutant of interest as described above.

For some studies it is desirable to produce recombinant hemoglobins carrying amino acid substitutions in both di-alpha and beta and in which the di-alpha subunits are genetically fused by a peptide linker so that a "di-hemoglobin" or "di-di-alpha" molecule is produced. Methods are described in WO 96/40920, incorporated herein by reference, for the construction of such "di-di-alpha" fusions to produce di-hemoglobins and these methods could be applied to construct di-di-alpha versions of any mutant alpha gene. Such di-di-alpha mutants could readily be combined with any beta mutant of interest as described above.

EXAMPLE 19

Small-scale Production for in vitro Kinetic Assays

For kinetic measurements on large numbers of hemoglobin variants *E coli* strains containing recombinant plasmids, such as derivatives of pSGE728, which encode variant hemoglobins were typically grown in shake flasks usually at volumes of about 50 ml. Generally defined media supplemented with about 0.2% yeast extract were used for cell growth and tetracycline was added, generally at 15 µg/ml to select for maintenance of the recombinant plasmid. Expression of the hemoglobin genes was induced by addition of IPTG, usually at a concentration of 100 µM and hemin was added to a final concentration of 50 µg/ml generally at the time of induction. Cells were generally grown and induced at 28° C. Cells grown to stationary phase, such as typical saturated overnight cultures, could be directly inoculated (generally at a dilution ranging from 1/50 to 1/1000) into media containing IPTG and hemin or such cultures could be inoculated into media lacking IITG and hemin, grown to log phase, e.g. 0.4–0.7 OD @ $A_{600}$ and then induced by the addition of IPTG with hemin typically being added to the cultures at the time of induction. Cultures were generally grown under inducing conditions overnight (~14–20 hours) although shorter times, e.g. about 6 hours could also be employed. At the end of this time, cells were pelleted by centrifugation and the cell pelleted were either frozen and stored at −80° C. or processed immediately.

Recombinant hemoglobins were purified by small-scale column chromatography using Fast Flow Zn-Chelating Sepharose (Pharmacia). During the purification, cells, lysates, all buffers and eluted hemoglobins were kept cold on ice as much as possible. Typically, a pellet of a 50 ml culture was resuspended with 1.0 ml ice-cold 25 mM sodium tetraborate and transferred to a 1.7 ml eppendorf tube. Cells were usually lysed by sonication, although enzymatic lysis by lysozyme could also be employed. Sonicated lysates were clarified by centrifugation (generally about 14,000×g for 15–20 minutes at 4° C.) following addition of 20 ul of 20 mM ZnAcetate. Supernatants were loaded onto a ~150–200 ul column that had previously been equilibrated as follows:

2–10 column volumes 0.5 M NaOH

6–10 column volumes 0.5 M NaCl, 20 mM Tris-HCl pH 8.1@0° C.

3–10 column volumes 20 mM ZnAcetate

6–10 column volumes 0.5 M NaCl, 20 mM Tris-HCl pH 8.1@0° C.

Following the loading, the column was washed with at least 9 column volumes 0.5 M NaCl, 20 mM Tris-HCl pH 8.1 at 0° C. followed by at least 3 column volumes 0.05 M NaCl, 20 mM Tris-HCl pH 8.1 at 0° C. and then eluted with ~1.0 ml of the desired buffer (e.g. 0.1 M Na phosphate pH 7.0) containing 30 mM EDTA. Hemoglobin was typically recovered in a volume of ~200–400 ul. These samples were used in kinetic assays such as NO oxidation and $O_2$ dissociation. If not used immediately, samples were frozen and stored −80° C.

EXAMPLE 20

Purification of Heme Pocket Mutants

All molecules, monomeric and dimeric, were first captured by immobilized metal affinity chromatography (IMAC) and further processed as described in WO 96/15151, incorporated herein by reference. The hemoglobin solution was then diafiltered into the appropriate load buffer for further purification. For monomeric hemoglobins, the appropriate load buffer was 20 mM Tris (pH 9.0) for loading onto an anion exchange column (Q Sepharose FF, Pharmacia, Uppsala, Sweden). The protein which was loaded onto the column at 15 gm/L is washed with three column volumes of 12.5 mM Tris (pH 7.8). The protein is then eluted in two to three volumes of 12.3 mM Tris (pH7.6) or if the pI of the protein is below 7.5 it is eluted in a Bis-Tris buffer at the appropriate pH. pI was used to determine proper wash and elution conditions for each protein, both monomeric and dimeric. Certain mutations on the surface of some of the heme pocket mutants were found to effect this value. For dimeric hemoglobins, the appropriate load buffer was 10 mM KPi (pH 7.0) for loading onto a ceramic hydroxyapatite (CHT) column (BioRad) or 20 mM Tris (pH 8.0) for loading onto a hydrophobic interaction chromatography (HIC) column (BioRad). The protein is loaded onto the CHT column at 20 gm/L the column is then washed with eight column volumes of 30–40 mM KPi (7.0). Five column volumes of 85–90 mM Kpi (pH7.0) are used to elute the protein from the column. When the HIC column is used protein is loaded at 15 gm/L and the column is then washed with five column volumes of 1.2M Ammonium Sulfate/20 mM Tris (pH 8.0). The protein is eluted using 3 column volumes of 1M Ammonium Sulfate/20 mM Tris (pH 8.0). The wash steps for both CHT and HIC columns were developed to allow the monomeric hemoglobin to be eluted while leaving the di-hemoglobins and larger molecules bound to the column. Pools from either column are diafiltered to prepare for loading onto an anion exchange column. The anion exchange step is designed to wash away remaining monomeric hemoglobin from the di-hemoglobin yielding a di-hemoglobin pool that is 98% pure on a size basis. The anion exchange column is a Super Q 650M (TosoHass). The column is equilibrated with 20 mM Tris (pH9.0) and 15 gm/L of protein is loaded on the column. The column is then washed with three column volumes of 10–15 mM Tris (pH 7.6–7.8) and the protein is eluted in three column volumes of 15–30 mM Tris (pH 7.6–7.8) or if pH is between 7.3–7.6 then a Bis-Tris buffer is used. The protein from this point on is handled as described in WO 96/15151.

EXAMPLE 21

Measurement of Reaction Between oxyHb and NO

Nitric oxide gas was passed through a column of NaOH pellets and used to thoroughly flush a tonometer. Anaerobic buffer (0.1 M sodium phosphate, pH 7.4) was injected into the tonometer and equilibrated with the NO to make a stock solution. Dilutions of the stock solution were made in glass syringes containing anaerobic buffer. Time courses of the reaction of oxyhemoglobin with NO were collected at 420 and 402 nm using an Applied Photophysics stopped-flow device. Temperature was 20° C. Data were collected and analyzed using the software program !SX.17MV supplied by Applied Photophysics.

Substituted alpha and beta subunits having approximately equal values of $k'_{NO,ox}$ were combined into tetrameric hemoglobin constructs for use in animal models. These "paired-mutant" rHbs (e.g. rHb2, rHb3, and rHb4; Table 20) were constructed with a genetically fused, mutated di-alpha subunit to prevent dissociation of the hemoglobins into alpha/beta dimers as described above. In Table 2, the mutations are designated, for example, as βN108K, which means the native human beta globin sequence residue number 108, with wildtype Asn (N) replaced by Leu (K).

TABLE 20

| rHb | description | ΔMAP (mm Hg) | $k_{NO,ox}$ ($\mu M^{-1}s^{-1}$) | $P_{50}$ (mm Hg) | $k_{autoox}$ ($h^{-1}$) |
| --- | --- | --- | --- | --- | --- |
| rHb1.1 | rHb0.1 + βN108K | 25.8 ± 2.0 | 58 | 32 | 0.051 |
| rHb0.1 | wild-type + dialpha fusion | 28.4 ± 5.7 | 58 | 10 | 0.042 |
| rHb Bethesda | rHb0.1 + βY145H | 24.1 ± 2.7 | 56 | 2.7 | 0.041 |
| rHb2 | rHB0.1 + αV62F/βV67F/βL106I | 19.3 ± 3.4 | 24 | 4.0 | 0.089 |
| rHb3 | rHb0.1 + αV62L/βV67F | 13.0 ± 1.6 | 15 | 3.4 | 0.10 |
| rHb4 | rHb0.1 + αL29F/βV67W | 7.6 ± 1.0 | 2 | 5.2 | 0.072 |

Figure 7:
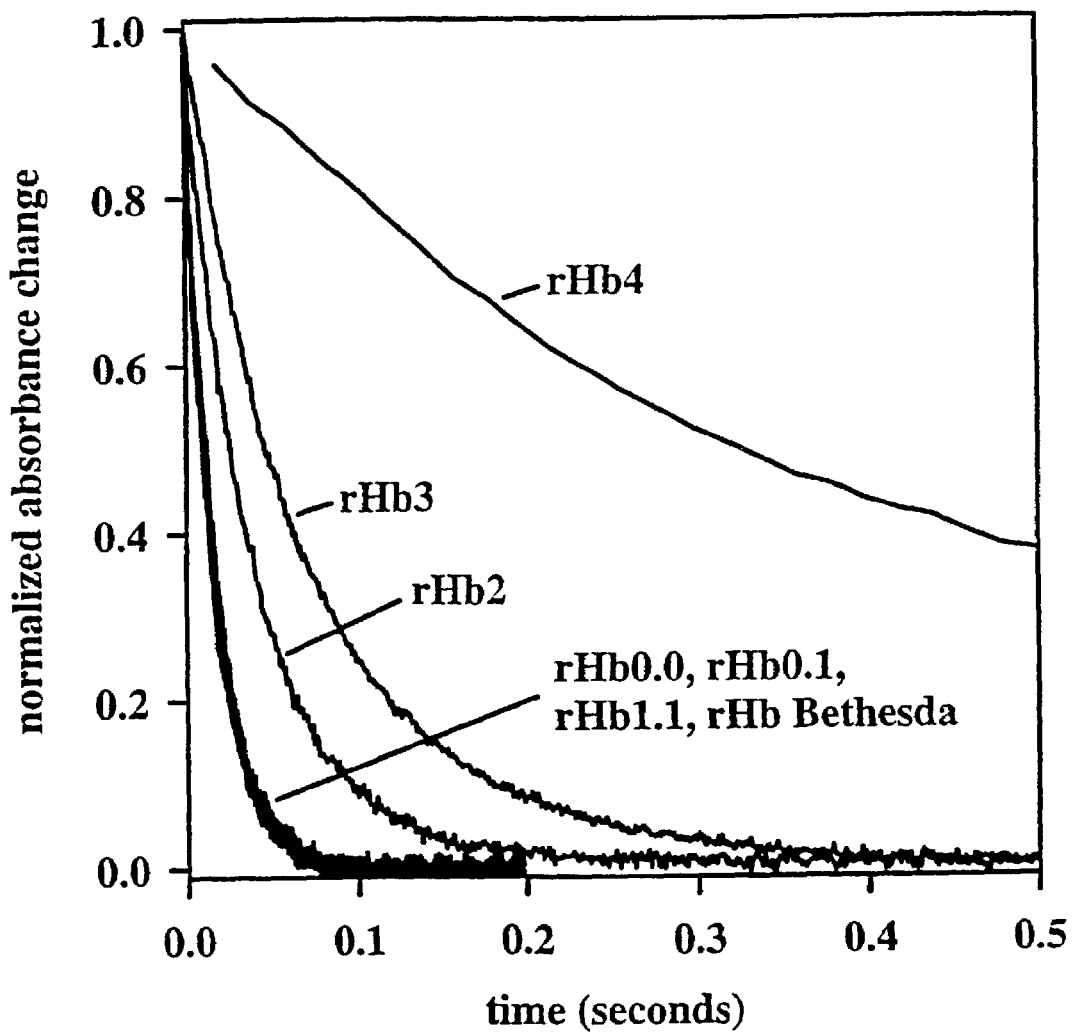
FIG. 7 shows the normalized time course of the NO-induced oxidation of recombinant oxyhemoglobin. The recombinant hemoglobin constructs rHb0.0, rHb0.1, rHb 1.1 and rHb Bethesda all have wild-type amino acids in their heme pockets and an NO-oxidation rate constant of 60 $\mu M^{-1}s^{-1}$. Distal heme pocket mutants rHb2, rHb3 and rHb4 have rate constants of 24, 15 and 2 $\mu M^{-1}s^{-1}$, respectively. Conditions after mixing were 0.2 μM oxyhemoglobin (heme), 1.0 μM NO, 20° C. The heme pocket substitutions in rHb2 are αE11(Val→Phe), βE11(Val→Phe), βG8 (Leu→Ile). In rHb3 the substitutions are α E11(Val→Leu), βE11(Val→Phe) and in rHb4 they are β B10(Leu→Phe), β E11(Val→Trp).

The resulting recombinant oxyhemoglobins have monophasic reactions with nitric oxide (FIG. 7), simplifying interpretation of in vivo experiments by having only one rate constant to consider. The values of $k'_{NO,ox}$ for rHb2, rHb3, and rHb4 are 24, 15, and 2 $\mu M^{-1}s^{-1}$, respectively. Recombinant hemoglobins rHb1.1, rHb0.1 (des val, di-α), rHb0.0 (des val, wildtype type), and rHb Bethesda have a wide range of $P_{50}$ values (32, 10, 15, and 2.7 mm Hg, respectively) due to different tendencies to form the low-affinity T-state quaternary structure. However, the latter four proteins have wild-type amino acids in the heme pockets and identical high values of the rate of NO-induced oxidation (~60 $\mu M^{-1}s^{-1}$) The data suggest that, regardless of the position of the allosteric (R/T) equilibrium, only substitutions within the heme pocket affect the NO reactivity of oxyhemoglobin.

All three of the paired-mutant hemoglobins have oxygen dissociation curves that are significantly left-shifted compared to rHb1.1 (Table 20). The low values of $P_{50}$ simplify interpretation of blood-pressure experiments by minimizing the formation of deoxyhemoglobin. In experiments with top-load administration and a normal complement of red blood cells, these high-affinity hemoglobins will remain nearly 100% oxygen-saturated throughout the circulation. Therefore, only the reactions of oxyhemoglobin with NO need be considered. For rHb1.1, the rate of NO binding to deoxyhemoglobin is similar to the rate of NO reaction with oxyhemoglobin, so the two forms of rHb1.1 have similar ability to scavenge NO. Generally, the rate of NO-induced oxidation is very similar to that for NO binding to the deoxy forms of myoglobins and hemoglobins, since the rate-limiting step in both processes is ligand entry into the distal pockets (Eich et al., supra.).

Tables 21 and 22 provide additional NO binding data for various mutant hemoglobins.

TABLE 21

| Strain | Description | $k'_{NO,OX}$ ($\mu M^{-1}s^{-1}$) | $k_{O2}$ ($s^{-1}$) | $P_{50}$ (mmHg) | $n_{max}$ |
| --- | --- | --- | --- | --- | --- |
| SGE3004 | diαV62L/βV67F | 15 | 2/6 | 4.5 | 1.85 |
| SGE3005 | 3004 + St. Mande | 15 | 6/43 | 8.6 | 1.38 |
| SGE3263 | 3004 + Prov. + Presby. | 15 | | 13.4 | 1.64 |
| SGE3173 | di-di 3004 | 13 | | | |
| SGE2821 | diαL29F, H58Q/βL106W | 12 | 12/30 | 42 | 1.7 |

TABLE 21-continued

| Strain | Description | k'$_{NO,OX}$ ($\mu M^{-1}s^{-1}$) | k$_{O2}$ ($s^{-1}$) | P$_{50}$ (mmHg) | n$_{max}$ |
|---|---|---|---|---|---|
| SGE3006 | 2821 + Prov + St. Mande | 13 | | ~100 | 1.83 |
| SGE3007 | 2821 + Prov + Pres | 13 | 8/25/80 | ~100 | 1.7 |
| SGE2822 | di-di 2821 | 11 | 13/32 | | |
| SGE1738 | 2822 + Pres | | | | |
| SGE3001 | diαL29F/βV67W | 1.5/4 | 0.3/4 | 6 | 1.63 |
| SGE1728 | 3001 + Pres | 1.2/5.5 | 0.3/2/21 | | |
| SGE1729 | 3001 + Prov | 1/4 | 0.3/2/10 | | |
| SGE3011 | diαL29W,H58Q/βv67W | 1.5/5 | 4/15 | 46 | 1.3 |
| SGE3010 | 3011 + Prov | 1.5/5 | 6/20 | 52 | 1.43 |
| SGE2966 | 3011 + Pres | | | | |
| SGE2968 | 3011 + Prov + Pres | 1.6/5.5 | | 114 | 1.89 |
| SGE2967 | 3011 + St. Mande | 2.5/10 | | 75 | 1.60 |
| SGE2963 | di-di 3011 | | | 37 | 1.13 |
| SGE2971 | di-di 3011 + Prov | 1.5/5 | 6/20 | 42.8 | 1.23 |
| SGE2969 | di-di 3011 + Pres | | | | |
| SGE2972 | di-di 3011 + Prov + Pres | | | | |
| SGE2970 | di-di 3011 + St. Mande | | | | |
| SGE3012 | diαL29W,H58Q/βL106W | 2/9 | | 87 | 1.57 |

In Table 21, the values for k'$_{nox,ox}$ ($\mu M^{-1}s^{-1}$) and k$_{O2}$ ($S^{-1}$) are in some cases expressed as two values (e.g., 2/6), which reflects the range of results that were sometimes obtained during analysis of these mutant combinations.

TABLE 22

| Subunit | Name | k'$_{NO,OX}$ ($\mu M^{-1}s^{-1}$ at 20° C.) | k$_{O2}$ ($s^{-1}$ at 20° C.) |
|---|---|---|---|
| αwild type | 1483 (rHb0.0) | 60 | 10 |
| α(B10)L29F | A51 | 3 | 0.2 |
| αL29F/αH58Q | 1733 (3341 di*) | 14 | 9 |
| α(B10)L29W | A57 | 3 | ~2 |
| αL29W/αH58Q | (3350 diα) | 2.7 | 8 |
| α (B10)L29A | 3159 | ~w.t. | 8 |
| α(E11)V62F | αE11 #10 | 26 | 4 |
| α(E11)V62W | αE11 #6 | 22 | 4 |
| α(E11)V62L | αE11 #7 | 16 | 4 |
| α(G8)L101I | | | |
| α(G8)L101F | HB9, HB12 | w.t. | |
| α(G8)L101W | HB1, HB5 | w.t. | |
| β wild type | 1483 (rHb0.0) | 60 | 35 |
| β(B10)L28F | AS4 | w.t. | |
| β(B10)L28W | AS6 | w.t. | |
| β(E11)V67F | 1725 (JD16αβ) | 12 | 3 |
| β(E11)V67W | 3313 (NS2) | 6-5 | 3 |
| βV67W/βH63Q(βK82D) | 1735 | .3/3 | 2/20 |
| βV67W/βH63A(βK82D) | 1734 | | |
| β(E11)V67L | 1724 (JD15 sm) | 16 | 24 |
| β(G8)L106I | 1727 (JD18 sm) | 60 | 45 |
| β(G8)L106F(βN108K) | 1723 (JD4 sm) | 30 | 60 |
| β(G8)L106W | 3267 ) | 30 | 60 |
| βV67W/βL106M | JD1 | 12 | |
| βV67L/βL106F | JD7 | 17 | |
| βV67F/βL106I | JD9 | 24 | 3 |
| βV67W/βL106M | JD11 | 24 | |
| βV67F/βL106W | JD16 | w.t. | ~5 |
| βV67W/βL106I | JD18 | 10 | ~5 |
| βV67F/βL106M | EV1 | 25,5 | 2 |
| βV67M/βL106F | EV2 | 0.8,3 | 40,1.4 |

"w.t." indicates that the mutant was not distinguishable from rHb0.0

EXAMPLE 22

Hemodynamic Data

Hemodynamic responses to hemoglobin administration were obtained in conscious, unrestrained rats. Male Sprague-Dawley rats were chronically instrumented with indwelling arterial and venous catheters at least 48 hours prior to experimentation. Top-load doses of 350 mg/kg of the rHb solutions (5 g/dl) were administered to separate groups of rats via intravenous infusion at a rate of 0.5 ml/min. Human serum albumin (HSA, 5 g/dl) was administered to another group of rats as a volume control. Arterial pressure was monitored continuously for 30 minutes prior to and 90 minutes following administration. All data are shown as mean ± standard error. Statistical comparisons between rHb1.1 and the other hemoglobins or HSA were made by repeated measures analysis of variance, p-values $\leq 0.05$ were considered significant.

Figure 8:
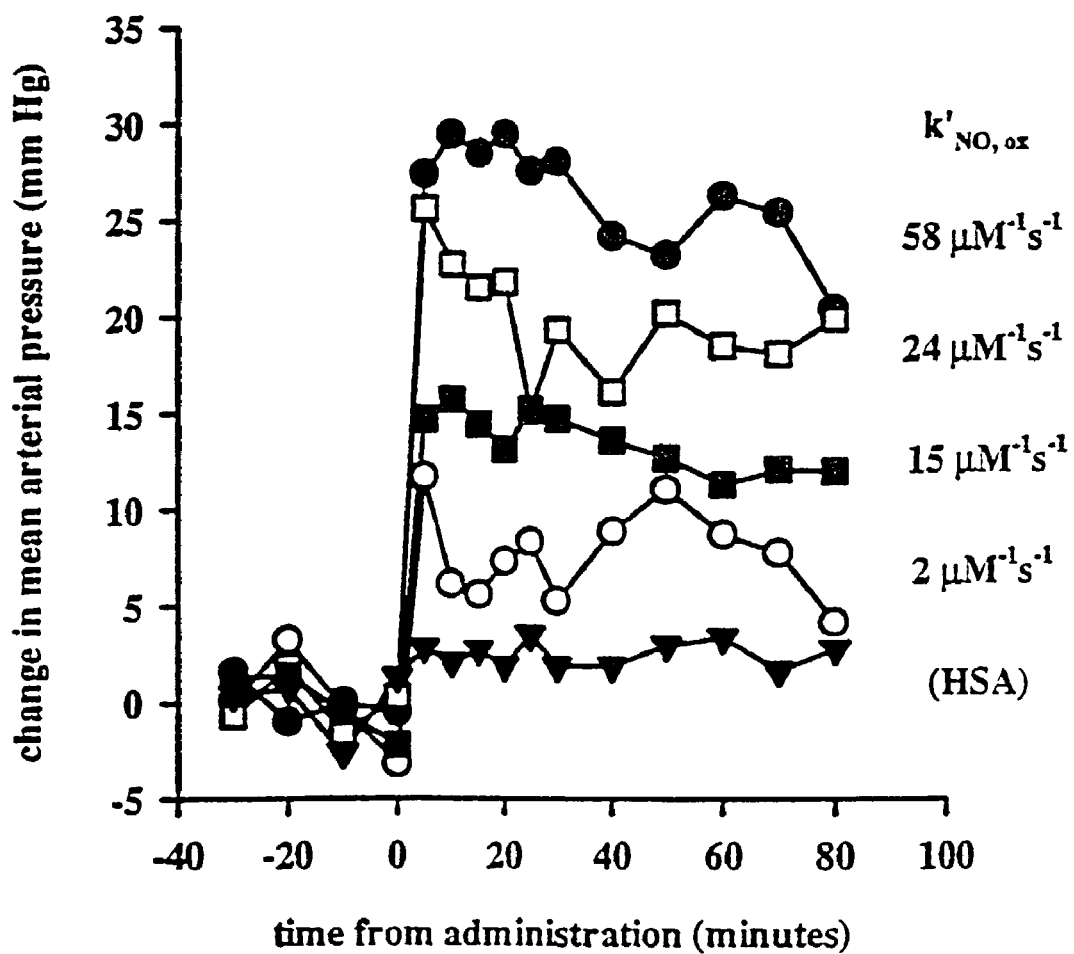
FIG. 8 shows the pressor effects of recombinant hemoglobins and human serum albumin (HSA). Changes in mean arterial pressure from pre-administration values are plotted versus time from administration. All hemoglobins contained a genetically fused dialpha subunit to prevent dissociation into αβ dimers. The rate constant for reaction of nitric oxide with each rHb is noted beside each data set. HSA indicates the pressor data collected when 5% HSA was administered as a volume control. Protein doses were 350 mg/kg for each rHb. rHb1.1 (●,n=6), rHb2 (□, n=6), rHb3 (■, n=6), rHb4 (0, n=6), 5% HSA (▲, n=9).
Figure 9:
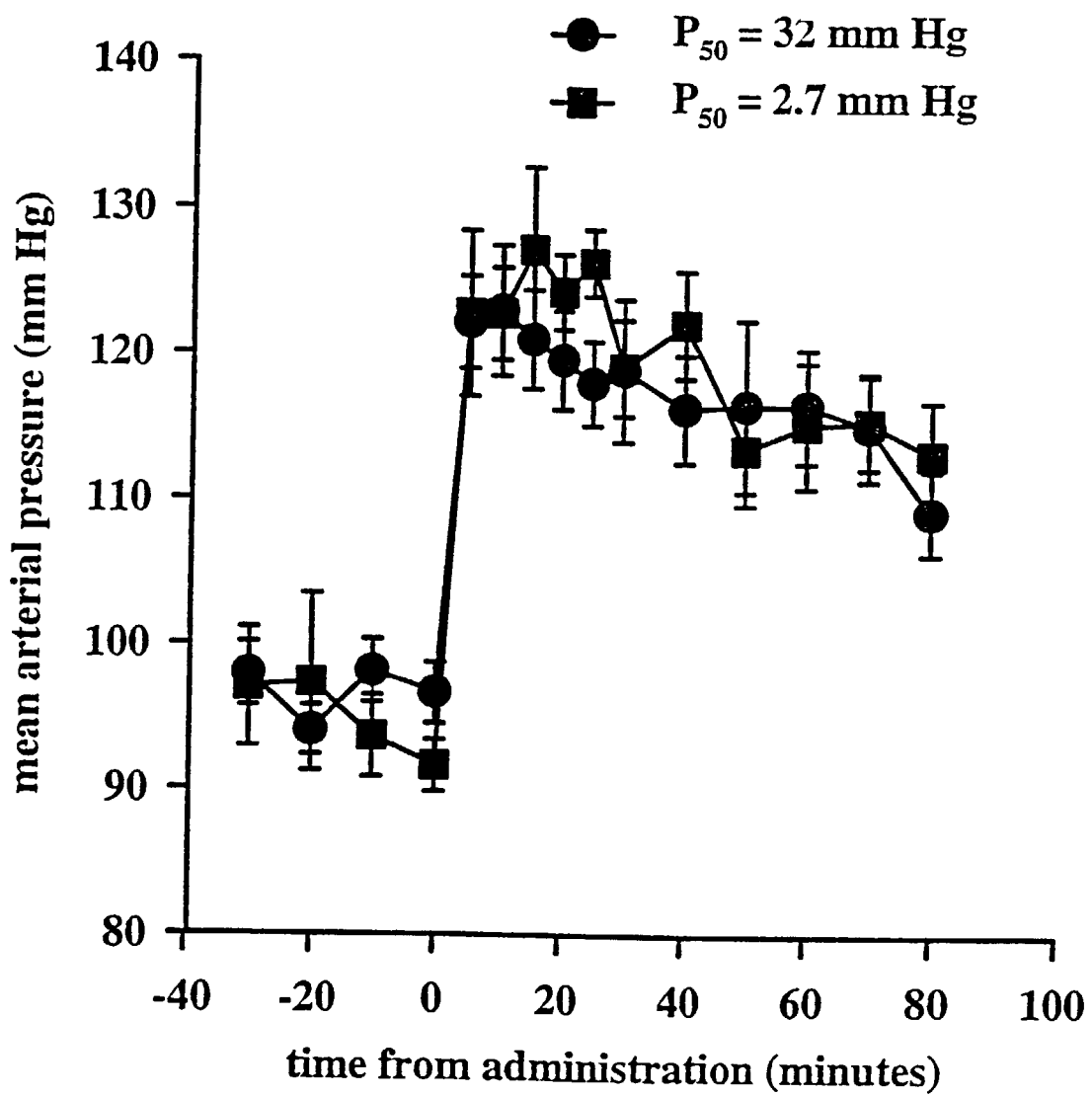
FIG. 9 shows the pressor responses to rHb 1.1 and rHb Bethesda. Both molecules contained a genetically fused dialpha subunit to prevent dissociation into alpha/beta dimers. Mean arterial pressure data are plotted versus time from administration. rHb1.1 has a $P_{50}$ of 32 mmHg, and rHb Bethesda has a $P_{50}$ of 2.7 mmHg. Both hemoglobins have a value of about 60 $\mu M^{-1}s^{-1}$ for the rate of NO oxidation, $k'_{NO,ox}$. Circles (●) represent data for rHb1.1 (n=6), and squares (■) denote data for rHb Bethesda (n=6). The two hemoglobins have identical rates of reaction with NO but significantly different $P_{50}$.

The mean arterial pressure (MAP) responses elicited by rHb1.1 and each of the three paired-mutant rHbs were determined in conscious rats (FIG. 8). The magnitude of the pressor response decreased as the rate constant for NO scavenging was decreased. At the lowest rate of NO oxidation, the pressor response was nearly as low as that observed following administration of an equivalent volume of 5% human serum albumin (HSA). These effects were not due simply to the low P$_{50}$ values for the distal pocket mutants, as shown in FIG. 9. The pressor effect of rHb1.1 (P$_{50}$=32 mm Hg) was identical to that of rHb Bethesda, which had a P$_{50}$ value (2.7 mm Hg) lower than any of the other hemoglobins in this study.

These results (Table 20, FIGS. 8 and 9) indicate that O$_2$ delivery to arteriolar smooth muscle or parenchyma tissue is unlikely to be the mechanism of the observed pressor effect. The P$_{50}$ of rHb Bethesda is low enough that this hemoglobin is essentially incapable of delivering oxygen to normal tissues, in top-load experiments where a normal complement of erythrocyte hemoglobin is present and maintains normal tissue pO$_2$ levels. However, rHb Bethesda elicits a pressor response identical to that of rHb1.1, which has a high P$_{50}$ and is capable of oxygen delivery. rHb0.1 has a similar pressor effect and an intermediate P$_{50}$ (Table 20). The results indicate that the mechanism of the pressor response is depletion of nitric oxide, not excessive oxygen delivery to arterioles. The changes in blood pressure correlate with the rates of NO-induced oxidation but not with oxygen affinity (Table 20).

The autoxidation rate of each hemoglobin was determined to examine the hypothesis that NO scavenging is mediated by methemoglobin (Alayash et al., *Mol. Med. Today* 1: 122–127 (1995); Alayash et al., *Arch. Biochem.*

Biophys 303: 332–338 (1993)). There is no correlation between autooxidation rates and pressor responses (Table 20), making it unlikely that the production of methemoglobin (or the concomitant generation of superoxide radical) is responsible for the increase in blood pressure. All of the autooxidation rates fall within a narrow range, with the largest value only about 2-fold greater than the smallest. rHb4 has the least effect on blood pressure but has an intermediate rate of autooxidation. Furthermore, the process of autooxidation is quite slow, with in vitro half-times greater than 6 hours at 37° C., while the pressor response reaches a maximum in only 5–10 minutes.

Figure 10:
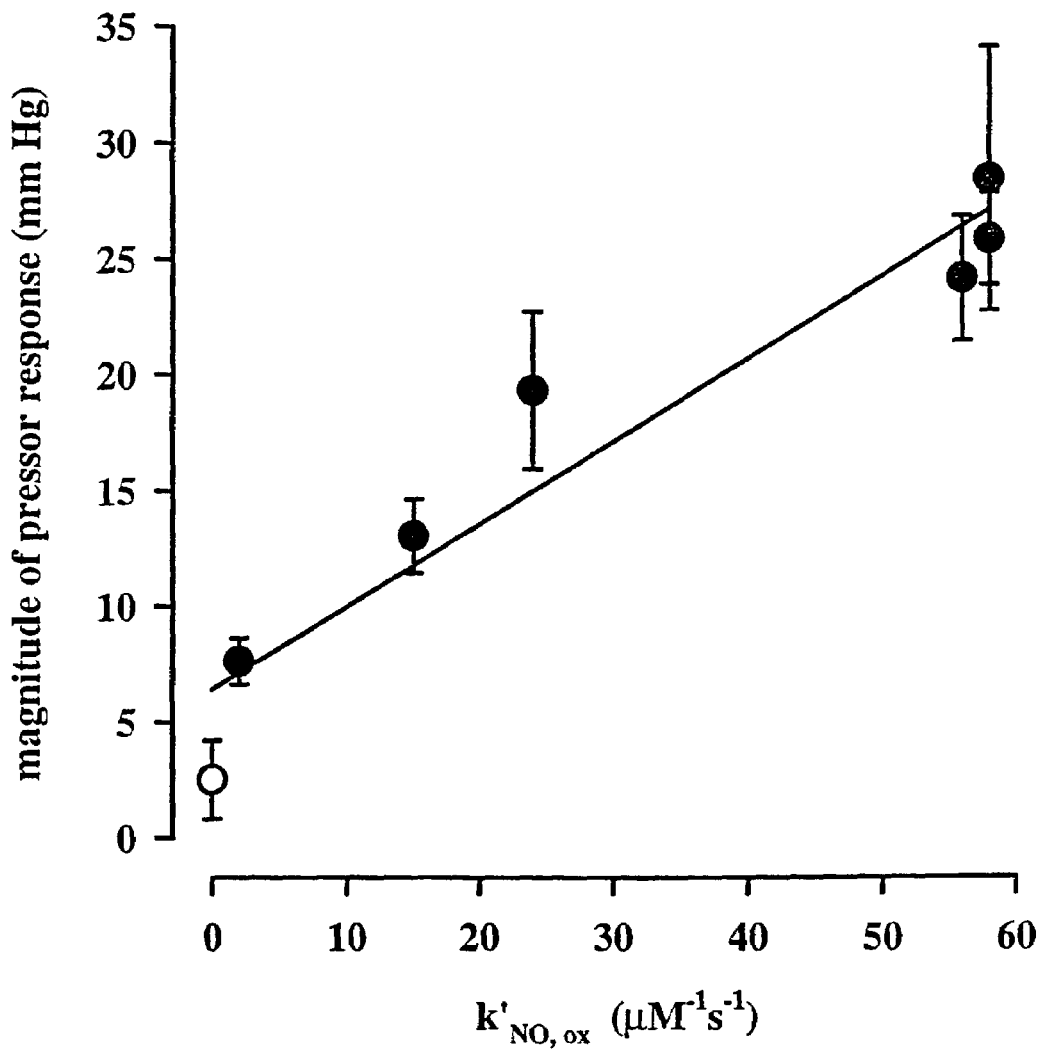
FIG. 10 shows the direct relationship between the magnitude of the pressor response and the rate of NO oxidation. The magnitude of the pressor response was calculated by averaging the post-infusion values for each time course in FIG. 8, and plotted against the measured value of $k'_{NO,ox}$ for the corresponding hemoglobin. The data point at the y-intercept was collected following administration of an equivalent volume of 5% HSA.

For each timecourse in FIG. 8, the post-infusion blood-pressure data were averaged, and the results were plotted against the value of NO-induced oxidation. As shown in FIG. 10, there is a direct relationship between the magnitude of pressor response and the rate of nitric oxide oxidation. The graph indicates that nitric oxide scavenging activity can account for nearly all of the pressor response of extracellular hemoglobin. If the value obtained for the albumin volume control is taken as the lower limit, there is very little pressor response remaining when the rate of NO-induced oxidation is extrapolated to zero. These results suggest strongly that the fundamental mechanism of the pressor response is reaction of nitric oxide in the distal heme pockets of oxy- and deoxyhemoglobin.

Therefore, it has been shown that the rate of reaction of hemoglobin with nitric oxide can be lowered significantly by replacing native distal heme pocket residues with larger, hydrophobic amino acids. The reactivity of NO toward both alpha and beta subunits can be controlled by this strategy. In contrast, amino acid substitutions outside the region of the heme pockets, some of which affect oxygen affinity, appear to have no effect on the oxidative reaction with NO. Similarly, fusion of the alpha subunits to stabilize the tetrameric form of hemoglobin has no effect on NO reactivity, as the value of NO-induced oxidation for rHb0.0 is the same as those for rHb0.1 and rHb1.1.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

The invention claimed is:

1. A method of obtaining high expression of soluble recombinant hemoglobin, comprising:

(a) incorporating into providing a host cell a vector containing a gene nucleotide sequences encoding globins capable of associating to form a functional hemoglobin, wherein the nucleotide sequence encoding a β globin having at least one mutation or combination of mutations that directs high soluble expression of the recombinant hemoglobin selected from the group consisting of:

D73Y;
D73I;
D73M;
D73E;
D73T;
D73K;
D73L;
K82D;
K82E;
K82G;
K82P;
K82Q;
K82S;
K82N;
K82H;
N102A;
N102V;
K82D(Providence)+D73G(Tilburg);
K82D(Providence)+D73Y(Vancouver);
V67W+D73E;
V67W+D73I;
V67W+D73Y(Vancouver);
V67W+D73E+K82D;(Providence)
V67W+D73I+K82D;(Providence)
V67W+D73Y(Vancouver)+K82D;(Providence);
V67W+K82E; and
V67W+K82G (b) inducing the host cell to express soluble recombinant hemoglobin; and (c) purifying the soluble recombinant hemoglobin.

2. The method of claim 1, further comprising adding excess hemin in step (b).

3. The method of claim 1, wherein said mutation is selected from the group consisting of D73I, D73M, D73E, D73T, D73Y, K82D, K82E, K82G, K82P, K82Q, K82S, K82N, N102A and N102V.

4. A method of obtaining high expression of soluble recombinant hemoglobin wherein at least one β globin of the recombinant hemoglobin has at least one mutation or combination of mutations selected from the group consisting of D73Y, D73I, D73M, D73E, D73T, D73K, D73L, K82D, K82E, K82G, K82P, K82Q, K82S, K82N, N102A, N102V, K82D(Providence)+D73G(Tilburg), K82D(Providence)+D73Y (Vancouver), V67W+D73E, V67W+D73I, V67W+D73Y (Vancouver), V67W+D73E+K82D V67W+D73I+K82D(Providence), V67W+D73Y (Vancouver)+K82D (Providence), V67W+K82E, and V67W+K82G, comprising:

(a) adding excess hemin to a culture of a host cell capable of expressing the soluble recombinant hemoglobin;

(b) inducing the host cell to express the soluble recombinant hemoglobin; and (c) purifying the soluble recombinant hemoglobin.

5. The method of claim 4, wherein the recombinant hemoglobin comprises at least one beta globin mutation or a combination of beta globin mutations selected from the group consisting of:

D73Y;
D73I;
D73M;
D73E;
D73T;
K82D;
K82E;
K82G;
K82P;
K82Q;
K82S;
K82N;
N102A; and
N102V.

6. The method of claims 2 or 4, wherein at least a 3-fold molar excess of heme is added.

* * * * *

UNITED STATES PATENT AND TRADEMARK OFFICE
CERTIFICATE OF CORRECTION

PATENT NO. : 7,049,406 B2 Page 1 of 1
APPLICATION NO. : 10/107871
DATED : May 23, 2006
INVENTOR(S) : Michael J. Weickert et al.

It is certified that error appears in the above-identified patent and that said Letters Patent is hereby corrected as shown below:

On The Title Page, Item (75) reads: "Michael J Weickert, Christopher B Glascock, Antony J Mathews, Douglas D Lemon, Daniel H Doherty, John S. Olson" which should read --Michael J. Weickert, Christopher B Glascock, and Anthony J Mathews--.
(Petition to Correct Inventorship filed June 7, 2004)

Signed and Sealed this

First Day of April, 2008

JON W. DUDAS
*Director of the United States Patent and Trademark Office*